(12) United States Patent
Belmant

(10) Patent No.: US 7,683,045 B2
(45) Date of Patent: *Mar. 23, 2010

(54) CLASS OF γδ T CELLS ACTIVATORS AND USE THEREOF

(75) Inventor: Christian Belmant, Six-Fours-les-Plages (FR)

(73) Assignee: Innate Pharma S.A., Marseille (FR)

( * ) Notice: Subject to any disclaimer, the term of this patent is extended or adjusted under 35 U.S.C. 154(b) by 146 days.

This patent is subject to a terminal disclaimer.

(21) Appl. No.: 11/817,450

(22) PCT Filed: Mar. 21, 2006

(86) PCT No.: PCT/IB2006/001206

§ 371 (c)(1),
(2), (4) Date: Aug. 30, 2007

(87) PCT Pub. No.: WO2006/103568

PCT Pub. Date: Oct. 5, 2006

(65) Prior Publication Data

US 2008/0207568 A1  Aug. 28, 2008

Related U.S. Application Data

(60) Provisional application No. 60/663,726, filed on Mar. 22, 2005.

(51) Int. Cl.
*A61K 31/66* (2006.01)
*C07F 9/02* (2006.01)

(52) U.S. Cl. ...... 514/102; 558/152
(58) Field of Classification Search ...... 558/152; 514/102

See application file for complete search history.

(56) References Cited

U.S. PATENT DOCUMENTS

| | | | |
|---|---|---|---|
| 6,660,723 B1 | 12/2003 | Belmant et al. | |
| 7,101,711 B1 | 9/2006 | Belmant et al. | |
| 7,109,183 B2 | 9/2006 | Belmant et al. | |
| 7,399,756 B2 | 7/2008 | Jomaa et al. | |
| 7,432,253 B2 | 10/2008 | Belmant et al. | |
| 2006/0030546 A1 | 2/2006 | Jomaa et al. | |
| 2006/0194755 A1 | 8/2006 | Romagne et al. | |
| 2006/0241087 A1* | 10/2006 | Montero et al. | 514/129 |
| 2006/0287281 A1 | 12/2006 | Belmant et al. | |
| 2007/0218086 A1 | 9/2007 | Tiollier | |
| 2008/0249067 A1 | 10/2008 | Jomaa et al. | |

FOREIGN PATENT DOCUMENTS

WO  WO 02/083720 A2  10/2002
WO  WO 2004/050096 A2  6/2004

* cited by examiner

*Primary Examiner*—Rei-tsang Shiao
(74) *Attorney, Agent, or Firm*—Saliwanchik, Lloyd & Saliwanchik

(57) ABSTRACT

The present invention relates to a new class of compounds having γδ T cells activating properties referred to herein as angelyl or tiglyl phosphoesters, compositions comprising any of these compounds and methods for regulating an immune response in a subject comprising the step of administering these compounds.

42 Claims, 3 Drawing Sheets

US 7,683,045 B2

CLASS OF γδ T CELLS ACTIVATORS AND USE THEREOF

CROSS-REFERENCE TO RELATED APPLICATION

This application is the U.S. national stage application of International Patent Application No. PCT/IB2006/001206, filed Mar. 21, 2006, which claims the benefit of U.S. Provisional Patent Application No. 60/663,726, filed Mar. 22, 2005, the disclosures of which are hereby incorporated by reference in their entireties, including all figures, tables and amino acid or nucleic acid sequences.

FIELD OF THE INVENTION

The present invention relates to a new class of compounds having γδ T cells activating properties referred to herein as angelyl phosphoesters, compositions comprising any of these compounds and methods for regulating an immune response in a subject comprising the step of administering these compounds.

BACKGROUND

Most human peripheral blood γδ T cells express a γδTCR heterodimer encoded by Vγ9/Vδ2 genes, some NK-lineage receptors for MHC class I and almost no CD4 nor CD8. These cells have been shown to exhibit strong, non MHC-restricted, cytolytic activity against virus-infected cells (Poccia et al (1997), parasite-infected cells (Constant et al (1995)), or tumor cells (Fournie et Bonneville (1996)). These cells are also physiologically amplified in the context of several unrelated infectious diseases such as tuberculosis, malaria, tularemia, colibacillosis and also by B-cell tumors (for review see Hayday, 2000).

Beside their anti-infectious activity, it was shown in short term cytotoxicity assays that Vγ9/Vδ2 T cells are able to lyse a wide variety of tumor cell lines from very diverse origins: lymphoma and leukemia from B-cell, T-cell or myeloid lineages (Fisch et al., 2000; Selin et al., 1992; Sicard et al., 2001; Sturm et al., 1990; Zheng et al., 2001a), breast carcinoma (Bank et al., 1993), glioblastoma (Fujimiya et al., 1997; Yamaguchi et al., 1997), renal cell carcinoma (Choudhary et al., 1995; Kobayashi et al., 2001; Mitropoulos et al., 1994), nasopharyngeal carcinoma (Zheng et al., 2001b), lung adenocarcinoma (Ferrarini et al., 1996).

In microbes, Vγ9/Vδ2+ lymphocytes spontaneously recognize a structurally related set of nonpeptide antigens, referred to as natural phosphoantigens and alkylamines. In B cell tumors, the nature of antigens for the γδ T cells remains unidentified. Vγ9/Vδ2+ lymphocytes are also responsive to a variety of virally infected-, activated- or tumoral cell types without prior exposure. Again, in these situations, the responsible antigens remain unknown (for review see Fisch, 2000). It has been shown that, in vitro, Vγ9/Vδ2 2+ lymphocytes respond to synthetic drugs such as therapeutic aminobisphosphonates (reviewed in Espinosa, 2001), leading to their in vitro activation. Recognition of natural non-peptide antigens is mediated by the γδ TCR, through amino acid residues located on both Vγ9- and Vδ2-CDR3 regions. Although neither processing nor presentation by CD1 or MHC molecules is involved, Vγ9/Vδ2+ lymphocyte activation by non-peptide antigens appears to require cell-to-cell contact (Lang, 1995; Morita, 1995; Miyagawa, 2001, Rojas, 2002).

The stimulating bacterial antigens have been shown to be small non peptidic compounds classically referred to as phosphoantigens (Behr et al., 1996; Belmant et al., 2000; Constant et al., 1995; Poquet et al., 1998; Tanaka et al., 1995), owing to the presence of phosphate groups in most instances.

Vγ9/Vδ2 T cells can also be activated through endogenous metabolites (acting in the micromolar range) such as isopentenyl pyrophosphate or IPP (Espinosa et al., 2001b; Tanaka et al., 1995), which is produced through the conventional mevalonate pathway shared by both microorganisms and mammalian cells. Production of IPP in the latter cells can be up-regulated in situations of cell stress and transformation. In particular a recent study has reported a correlation between the endogenous production levels of IPP in tumor cells and their susceptibility to Vγ9/Vδ2 T cell-mediated lysis (Gober et al., 2003).

Also consistent with a direct contribution of endogenous metabolites of the mevalonate pathway to Vγ9/Vδ2 T cell recognition, cell treatment with pharmacological agents preventing IPP biosynthesis (such as statins) or leading to IPP accumulation (such as aminobisphosphonates, see below) lead respectively to decreased or enhanced Vγ9/Vδ2 T cell stimulating properties of the treated cells (Gober et al., 2003; Kato et al., 2001).

Aminobisphosphonates are thought to inhibit FPP synthase, an enzyme in the mevalonate pathway, the inhibition of which causes the accumulation and release of upstream isoprenoid lipids such as IPP. Aminobisphosphonate compounds had been used in human therapy for the treatment of bone metastases in cancer patients, and provided a first set of evidence for in vivo expansion of human Vγ9/Vδ2+ lymphocytes induced by phosphoantigen agonists, reporting increases of circulating γδ T cells within one to three weeks in human adults with multiple myeloma after therapeutic intravenous injection of 60-90 mg of pamidronate (Kunzmann et al, 1999). However, such compounds require presentation by antigen presenting cells and cannot produce substantial stimulation of Vγ9/Vδ2 T cell activity as assessed by cytokine secretion in a pure Vγ9/Vδ2 T cell culture. Moreover, pamidronate shows very low potency of activation of γδ T cells, reported to achieve at best only 2-fold increase in γδ T cell count (Wilhelm et al., 2003).

Recently, several highly potent γδ T cell activating pyrophosphate-containing compounds have been described which directly activate γδ T cells. In particular, phosphohalohydrin and phosphoepoxide compounds were described by the group of J. J. Fournie. (R,S)-3-(bromomethyl)-3-butanol-1-yl-diphosphate, also referred to as BrHPP (BromoHydrin Pyro-Phosphate) is currently used in ongoing human clinical studies to stimulate the proliferation of γδ T cells ex vivo. Other pyrophosphate containing compounds with high specific activity (EC50 in the nanomolar or better range) are produced through an isoprenoid biosynthetic pathway called the "Rohmer" or "non-mevalonate" pathway, which is specific to pro- and eukaryotic microorganisms (Feurle et al., 2002; Hintz et al (2003); Jomaa et al., 1999a; Jomaa et al., 1999b; Rohmer et al., 1993).

Despite the foregoing, there is still a need of new compounds providing γδ T cell activation, in particular compounds having increased potency and/or preferred pharmacodynamic properties. Such compounds have particular advantages in non-life threatening or chronic therapeutic indications where therapies should be free of toxicity.

SUMMARY OF THE INVENTION

The present invention now discloses a new class of compounds having γδ T cell activating properties. This new class of compounds is referred to as the angelyl and tiglyl phosphoester class. The inventors have found that the class of compounds described herein have high potency in comparison to other compounds known to modulate γδ T cell activity. Preferably the compounds of the invention are isolated, purified or partially purified.

These compounds can be used to efficiently regulate the activity of γδ T cells, particularly the activation and proliferation of γδ T cells, preferably Vγ9/Vδ2 T cells, in vivo in a subject. These new γδ T cell activators can be used in accordance with any of the methods described herein. These compounds are particularly suited for immunotherapy, particularly to treat a subject having a tumor or a subject suffering from other diseases, particularly an infectious disease, an autoimmune disease or an allergic disease. Compounds according to the present invention can also be used as a vaccine adjuvant.

Accordingly, the invention provides a γδ T cell activator of formula (I):

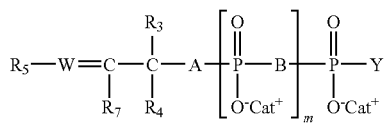

wherein Cat+ represents one (or several, identical or different) organic or mineral cation(s) (including proton);
m is an integer from 1 to 3;
B is O, NH, or any other group capable of being hydrolyzed;
A is O, NH, CHF, $CF_2$ or $CH_2$, or any other isosteric group;
W is $C-R_6$ or N;
$R_7$ is a $(C_1-C_3)$alkyl group or any other isosteric group such as $CF_3$;
$R_3$, $R_4$ and $R_6$, identical or different, are a hydrogen or a $(C_1-C_3)$alkyl group or any other isosteric group such as $CF_3$;
$R_5$ is an $(C_2-C_3)$acyl, an aldehyde, an $(C_1-C_3)$alcohol, or an $(C_2-C_3)$ester; and,
Y=O⁻Cat+, a $(C_1-C_3)$alkyl group, a group -A-R, wherein R is a linear, branched, or cyclic, aromatic or not, saturated or unsaturated, $C_1-C_{50}$ hydrocarbon group, optionally interrupted by at least one heteroatom, wherein said hydrocarbon group comprises an alkyl, an alkylenyl, or an alkynyl, preferably an alkyl or an alkylene, which can be substituted by one or several substituents selected from the group consisting of: an alkyl, an alkylenyl, an alkynyl, an epoxyalkyl, an aryl, an heterocycle, an alkoxy, an acyl, an alcohol, a carboxylic group (—COOH), an ester, an amine, an amino group (—$NH_2$), an amide (—$CONH_2$), an imine, a nitrile, an hydroxyl (—OH), an aldehyde group (—CHO), an halogen, an halogenoalkyl, a thiol (—SH), a thioalkyl, a sulfone, a sulfoxide, and a combination thereof.

Preferably, A is O or $CH_2$. More preferably, A is O. More preferably, $R_3$, $R_4$ and $R_6$ are a hydrogen. Preferably, $R_5$ is —$CH_2$—OH, —CHO, —CO—$CH_3$ or —CO—$OCH_3$. More preferably, $R_5$ is —$CH_2$—OH. Preferably, $R_7$ is $CH_3$ or an isosteric group thereof, such as $CH_2F$, $CF_2H$ or $CF_3$. Preferably, m is 1.

In one embodiment, the group $R_5$ and the moiety —$CR_3R_4$-A-[POOB]$_m$—POOY of formula (I) are in Z (or cis) configuration. In another embodiment, the group $R_5$ and the moiety —$CR_3R_4$-A-[POOB]$_m$—POOY of formula (I) are in E (or trans) configuration with respect to the double bond position. Insofar as it is observed herein (see Examples) that γδ T cell activator of formula (I) in which the group $R_5$ and the moiety —$CR_3R_4$-A-[POOB]$_m$—POOY are in Z configuration has significantly greater activity in the activation of γδ T cells than the E configuration, the Z configuration is preferred.

In one aspect, said activator is a compound selected from the group consisting of:
A compound of Formula (II):

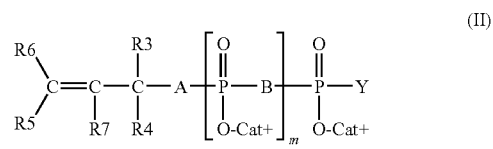

wherein Cat+, m, B, A, $R_5$, $R_3$, $R_4$, $R_6$, $R_7$, and Y are defined as in Formula (I).
A compound of Formula (III):

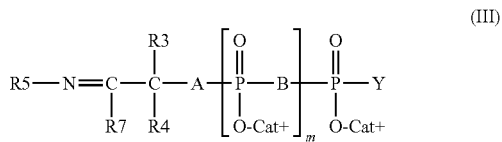

wherein Cat+, m, B, A, $R_5$, $R_3$, $R_4$, $R_7$, and Y are defined as in Formula (I).
A compound of Formula (IV):

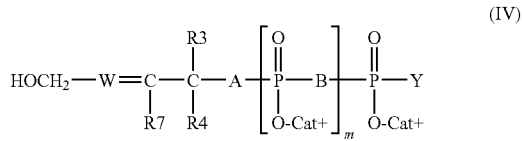

wherein Cat+, m, B, A, W, $R_5$, $R_3$, $R_4$, $R_6$, $R_7$, and Y are defined as in Formula (I).
A compound of Formula (V):

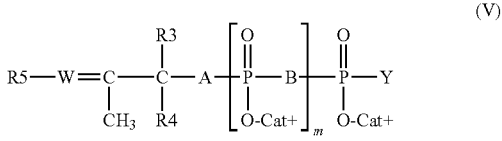

wherein Cat+, m, B, A, W, $R_5$, $R_3$, $R_4$, $R_6$, and Y are defined as in Formula (I).
A compound of Formula (VI):

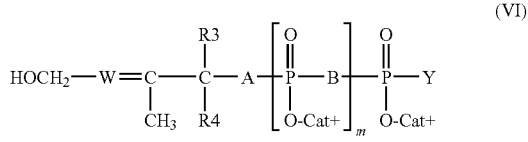

wherein Cat+, m, B, A, W, $R_3$, $R_4$, $R_6$, and Y are defined as in Formula (I).

A compound of Formula (VII):

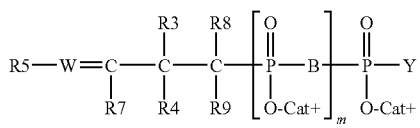
(VII)

wherein Cat+, m, B, W, $R_5$, $R_3$, $R_4$, $R_6$, $R_7$, and Y are defined as in Formula (I), $R_8$ is H or F, and $R_9$ is H or F.

A compound of Formula (VIII):

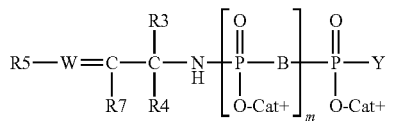
(VIII)

wherein Cat+, m, B, W, $R_5$, $R_3$, $R_4$, $R_6$, $R_7$, and Y are defined as in Formula (I).

A compound of Formula (IX):

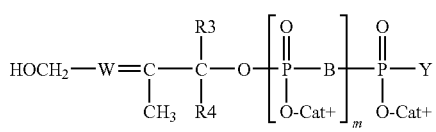
(IX)

wherein Cat+, m, B, W, $R_3$, $R_4$, $R_6$, and Y are defined as in Formula (I).

A compound of Formula (X):

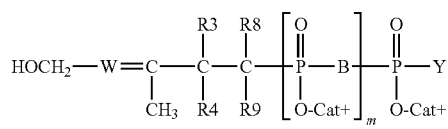
(X)

wherein Cat+, m, B, W, $R_3$, $R_4$, $R_6$, and Y are defined as in Formula (I), $R_8$ is H or F, and $R_9$ is H or F.

A compound of formula (XI):

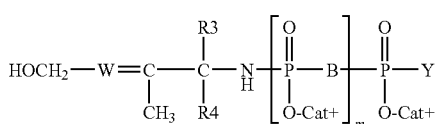
(XI)

wherein Cat+, m, B, W, $R_3$, $R_4$, $R_6$, and Y are defined as in Formula (I).

In a preferred embodiments, the γδ T cell activator is a compound of formula (XII) or (XII'):

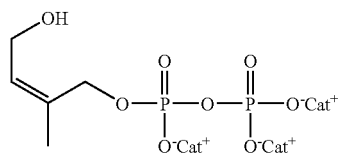
(XII)

(Z)-4-hydroxy-2-methylbut-2-enyl pyrophosphate (also referred to as HAngelylPP)

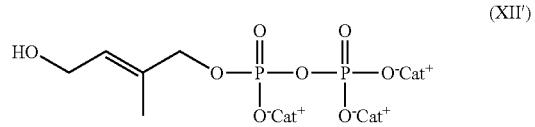
(XII')

(E)-4-hydroxy-2-methylbut-2-enyl pyrophosphate (also referred to as HTiglylPP)

In further preferred embodiments, the γδ T cell activator is a compound of formula (XIII) or (XIII'):

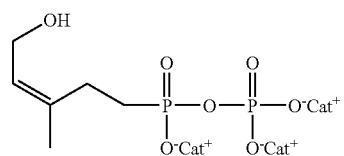
(XIII)

(Z)-5-hydroxy-3-methylpent-3-enyl pyrophospho-nate (also referred to as C-HAngelylPP)

(XIII')

(E)-5-hydroxy-3-methylpent-3-enyl pyrophospho-nate (also referred to as C-HTiglylPP)

In additional preferred embodiments, the γδ T cell activator is a compound of formula (XIV) or (XIV'):

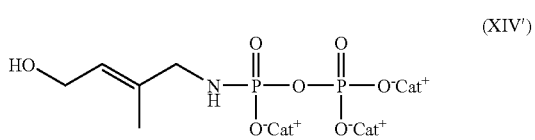
(XIV)

(Z)-4-hydroxy-2-methylbut-2-enyl pyrophosphora-midate (also referred to as N-HAngelylPP)

(XIV')

(E)-4-hydroxy-2-methylbut-2-enyl pyrophosphoramidate (also referred to as N-HTiglylPP)

In further embodiments, the γδ T cell activator is a compound of formula (XV):

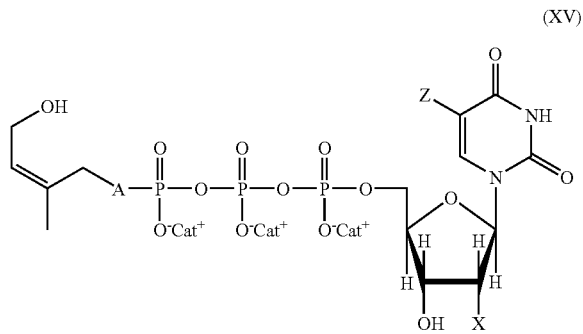

(XV)

wherein Cat+ and A are defined as in Formula (I); X is H and Z is CH$_3$ (deoxyribonucleoside is thymidine) or X is OH and Z is H (ribonucleoside is uridine). In one embodiment, the compound of formula (XVI) is in E (or trans) configuration. In a preferred embodiment, the compound of formula (XVI) is in Z (or cis) configuration.

The present invention also provides pharmaceutical composition comprising a γδ T cell activator according to any one of the embodiments described herein. In preferred embodiments, the Cat+ cation will be a pharmaceutically acceptable cation. Also provided are methods of modulating, preferably activating, a γδ T cell, the method comprising bringing a γδ T cell into contact with a γδ T cell activating compound described herein. As will be appreciated, compounds of the invention may be used to activate γδ T cell in vitro or in vivo. γδ T cells activated in vitro may be used in any suitable method following activation, including in therapy or prevention of disease. In one preferred example, activated γδ T cells are administered to a mammal, preferably a human. In a preferred aspect, the invention encompasses a method of treatment comprising (a) bringing a γδ T cell into contact with a γδ T cell activating compound described herein and (b) administering γδ T cells of step (a) to a subject. Methods for preparing γδ T cells for such applications are known in the art, for example can be carried out as described in US2005196385 and WO03070921, both by Romagne and Laplace, the disclosures of which are incorporated herein by reference.

Also provided are methods of modulating, preferably activating, a γδ T cell comprising administering to a subject a γδ T cell activator described herein. In preferred embodiments, the inventions provides a method for treating or preventing a disease comprising administering to a subject a γδ T cell activator described herein in an amount sufficient to ameliorate or prevent said disease. Also provided is the use of a γδ T cell activator of the invention for the manufacture of a pharmaceutical composition for regulating γδ T cells in a human subject, preferably thereby treating a disease. Preferably said disease is a tumor or proliferative disorder, an infectious disease, an autoimmune disease or an allergic disease.

Additional embodiments and details are further provided herein.

DETAILED DESCRIPTION

Definitions

Figure 1:
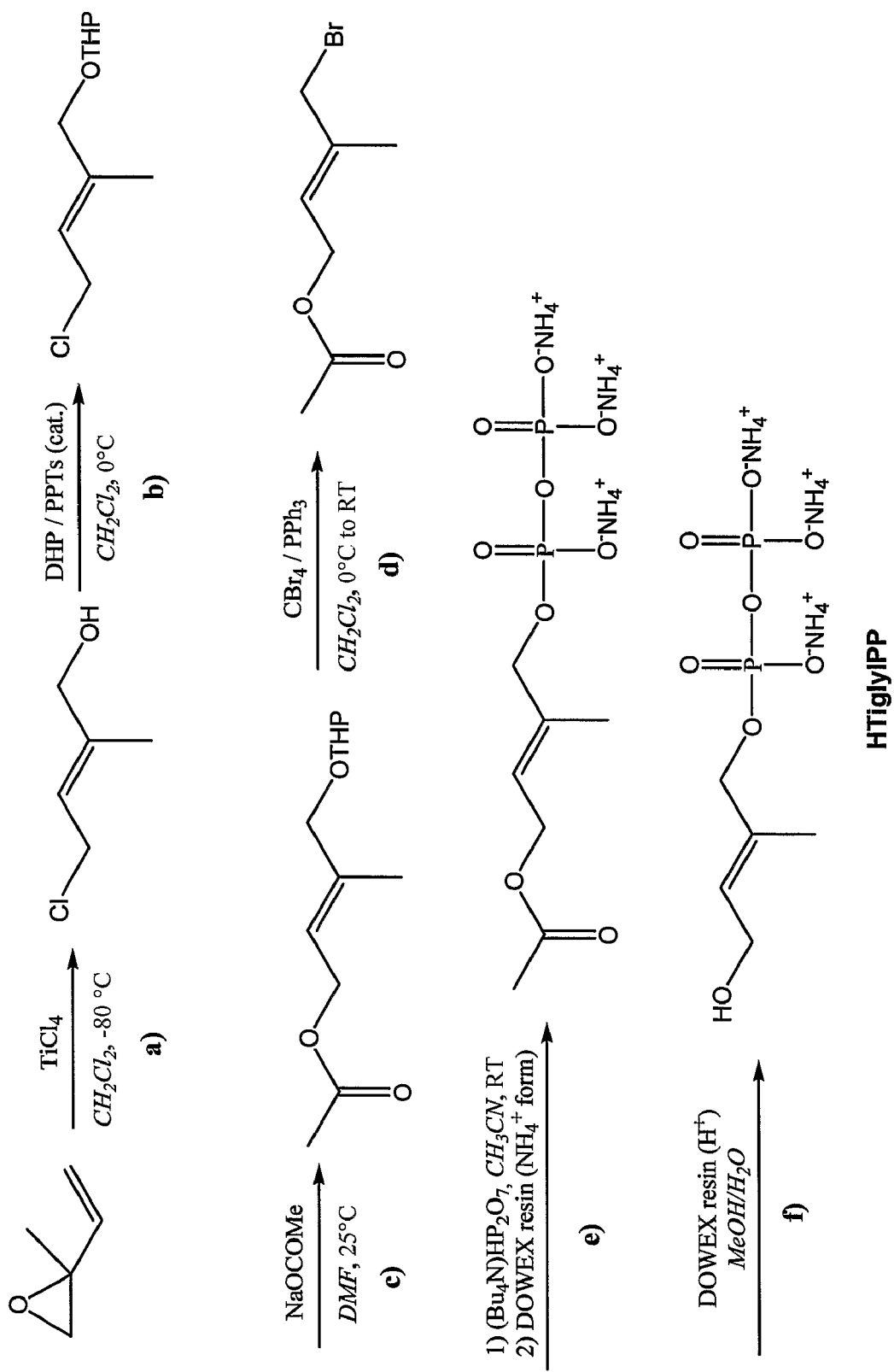
FIG. 1 is a synthetic scheme for the preparation of compound HTiglylPP as carried out in Example 1.

Within the context of the present invention, the expression "regulating the activity of γδ T cells" designates causing or favoring an increase in the number and/or biological activity of such cells in a subject. Regulating thus includes without limitation modulating (e.g., stimulating) expansion of such cells in a subject and/or, for instance, triggering of cytokine secretion (e.g., TNFα or IFNγ). As indicated, γδ T cells normally represent between about 1-10% of total circulating lymphocytes in a healthy adult human subject. The present invention can be used to significantly increase the γδ T cells population in a subject, particularly to reach at least 10%, 12%, 15%, 20%, or 30-90% of total circulating lymphocytes, typically 40-90%, more preferably from 50-90%. In typical embodiments, the invention allows the selective expansion of γδ T cells in a subject, to reach 60-90% of total circulating lymphocytes, preferably 70-90%, more preferably from 80-90%. Regulating also includes, in addition or in the alternative, modulating the biological activity of γδ T cells in a subject, particularly their cytolytic activity or their cytokine-secretion activity. The invention defines novel conditions and strategies for increasing the biological activity of γδ T cells towards target cells.

Where "comprising" is used, this can preferably be replaced by "consisting essentially of", more preferably by "consisting of".

Where hereinbefore and hereinafter numerical terms are used, they are meant to include the numbers representing the upper and lower limits. For example, "between 1 and 3" stands for a range "from and including 1 up to and including 3", and "in the range from 1 to 3" would stand for "from and including 1 up to and including 3". The same is true where instead of numbers (e.g. 3) words denoting numbers are used (e.g. "three").

Where "about" is used in connection with a number, this preferably means the number+/−15%, more preferably the number plus 5%, most preferably the number itself without "about". For example, "about 100" would stand for "from and including 85 to and including 115". Where "about" is used in connection with numeric ranges, for example "about 1 to about 3", or "between about one and about three", preferably the definition of "about" given for a number in the last sentence is applied to each number defining the start and the end of a range separately. Preferably, where "about" is used in connection with any numerical values, the "about" can be deleted.

"Weekly" stands for "about once a week" (meaning that more than one treatment is made with an interval of about one week between treatments), the about here preferably meaning +/−1 day (that is, translating into "every 6 to 8 days"); most preferably, "weekly" stands for "once every 7 days".

As used herein, the term "EC50" with respect to regulating the activity of γδ T cells, refers to the efficient concentration of the subject compositions which produces 50% of its maximum response or effect with respect to such activity of γδ T cells.

The term "isolated" refers to a compound or product that is refers to a compound which represents at least 30%, more preferably at least 50%, 60% or 70%, and most preferably at least 80%, 90%, 95% or 98% of the compound present in the mixture.

"Purified" phosphoantigen or phosphoantigen composition refers to substantially pure phosphoantigen, essentially pure phosphoantigen, or a salt thereof, or to phosphoantigen, or a salt thereof which is substantially free, essentially free, or free of another compound.

"Partially purified" phosphoantigen or phosphoantigen composition refers to phosphoantigen, or a salt thereof that is less than 90% pure.

New Class of γδ T Lymphocyte Activators: Angelyl and Tiglyl Phosphoesters

The new class of compounds described by the present inventors comprises angelyl and tiglyl phosphoesters. The inventors have found that the compounds of this class show significant potency over other compounds in modulating γδ T cell activity. The recognition of the angelyl phosphoester compounds by their biological target may involve an enzymatic processing of the compound. This processing is thought to rely on an intramolecular cyclization reaction concerted with the hydrolysis of the labile phosphate moiety (or energy release). The angelyl phosphoester compounds in Z isomer are predicted to favor the intramolecular cyclization, compared to the tiglyl phosphoester E isomer. Compounds of the angelyl phosphoester class may have increased potency (e.g. less compound needed, less likelihood of toxicity), or these compositions can provide distinct pharmacological properties, for example target binding affinity, ADME properties (absorption, distribution, metabolism and excretion) over previously known activators of γδ T cells. In further preferred embodiments, specific compounds of the invention are provided which may each have differing properties and can be used depending on the application sought. For example the compounds may differ as to in vivo stability, leading for example to different circulation half-lives or different maximal activation of γδ T cells.

The new class of γδ T lymphocyte activators according to the present invention comprises the compounds of formula (I):

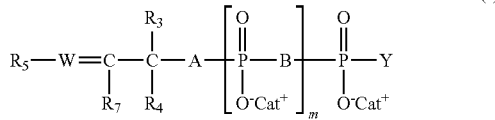

(I)

wherein Cat+ represents one (or several, identical or different) organic or mineral cation(s) (including proton);

m is an integer from 1 to 3;

B is O, NH, or any other group capable of being hydrolyzed;

A is O, NH, CHF, $CF_2$ or $CH_2$, or any other isosteric group;

W is C—$R_6$ or N;

$R_7$ is a ($C_1$-$C_3$)alkyl group or any other isosteric group such as $CF_3$;

$R_3$, $R_4$, and $R_6$, identical or different, are a hydrogen or a ($C_1$-$C_3$)alkyl group or any other isosteric group such as $CF_3$;

$R_5$ is an ($C_2$-$C_3$)acyl, an aldehyde, an ($C_1$-$C_3$)alcohol, or an ($C_2$-$C_3$)ester; and, Y=O⁻Cat+, a $C_1$-$C_3$ alkyl group, a group -A-R, wherein R is a linear, branched, or cyclic, aromatic or not, saturated or unsaturated, $C_1$-$C_{50}$ hydrocarbon group, optionally interrupted by at least one heteroatom, wherein said hydrocarbon group comprises an alkyl, an alkylenyl, or an alkynyl, preferably an alkyl or an alkylene, which can be substituted by one or several substituents selected from the group consisting of: an alkyl, an alkylenyl, an alkynyl, an epoxyalkyl, an aryl, an heterocycle, an alkoxy, an acyl, an alcohol, a carboxylic group (—COOH), an ester, an amine, an amino group (—$NH_2$), an amide (—$CONH_2$), an imine, a nitrile, an hydroxyl (—OH), a aldehyde group (—CHO), an halogen, an halogenoalkyl, a thiol (—SH), a thioalkyl, a sulfone, a sulfoxide, and a combination thereof.

An "isosteric group" refers to elements, functional groups, substitutents, molecules or ions having different molecular formulae but exhibiting similar or identical physical properties. For example, $CF_3$ is an isosteric group of $CH_3$. Typically, two isosteric groups have similar or identical volumes and shapes.

In a particular embodiment, Y can be a radical selected from the group consisting of a nucleoside, a nucleotide, an oligonucleotide, a nucleic acid, an amino acid, a peptide, a protein, a monosaccharide, an oligosaccharide, a polysaccharide, a fatty acid, a simple lipid, a complex lipid, a folic acid, a tetrahydrofolic acid, a phosphoric acid, an inositol, a vitamin, a co-enzyme, a flavonoid, an aldehyde, an epoxide and a halohydrin.

In one embodiment, the group $R_5$ and the moiety —$CR_3R_4$-A-[POOB]$_m$—POOY of formula (I) are in Z (or cis) configuration. In another embodiment, the group $R_5$ and the moiety —$CR_3R_4$-A-[POOB]$_m$—POOY of formula (I) are in E (or trans) configuration. Insofar as it is observed herein (see Examples) that γδ T cell activator of formula (I) in which the group $R_5$ and the moiety —$CR_3R_4$-A-[POOB]$_m$—POOY are in Z configuration has significantly greater activity in the activation of γδ T cells than the E configuration, the Z configuration is preferred.

In a particular embodiment, the substituents as defined above are substituted by at least one of the substituents as specified above.

Preferably, the substituents are selected from the group consisting of: an ($C_1$-$C_6$)alkyl, an ($C_2$-$C_6$)alkylenyl, an ($C_2$-$C_6$)alkynyl, an ($C_2$-$C_6$)epoxyalkyl, an aryl, an heterocycle, an ($C_1$-$C_6$)alkoxy, an ($C_2$-$C_6$)acyl, an ($C_1$-$C_6$)alcohol, a carboxylic group (—COOH), an ($C_2$-$C_6$)ester, an ($C_1$-$C_6$)amine, an amino group (—$NH_2$), an amide (—$CONH_2$), an ($C_1$-$C_6$) imine, a nitrile, an hydroxyl (—OH), a aldehyde group (—CHO), an halogen, an ($C_1$-$C_6$)halogenoalkyl, a thiol (—SH), a ($C_1$-$C_6$)thioalkyl, a ($C_1$-$C_6$)sulfone, a ($C_1$-$C_6$)sulfoxide, and a combination thereof.

More preferably, the substituents are selected from the group consisting of: an ($C_1$-$C_6$)alkyl, an ($C_2$-$C_6$)epoxyalkyl, an ($C_2$-$C_6$)alkylenyl, an ($C_1$-$C_6$)alkoxy, an ($C_2$-$C_6$)acyl, an ($C_1$-$C_6$)alcohol, an ($C_2$-$C_6$)ester, an ($C_1$-$C_6$)amine, an ($C_1$-$C_6$)imine, an hydroxyl, a aldehyde group, an halogen, an ($C_1$-$C_6$)halogenoalkyl, and a combination thereof.

Still more preferably, the substituents are selected from the group consisting of: an ($C_3$-$C_6$)epoxyalkyl, an ($C_1$-$C_3$) alkoxy, an ($C_2$-$C_3$)acyl, an ($C_1$-$C_3$)alcohol, an ($C_2$-$C_3$)ester, an ($C_1$-$C_3$)amine, an ($C_1$-$C_3$)imine, an hydroxyl, an halogen, an ($C_1$-$C_3$)halogenoalkyl, and a combination thereof.

Preferably, said hydrocarbon group is a ($C_3$-$C_{25}$)hydrocarbon group, more preferably a ($C_5$-$C_{10}$)hydrocarbon group.

In the context of the present invention, the term "alkyl" more specifically means a group such as methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl and the other isomeric forms thereof. ($C_1$-$C_6$)alkyl more specifically means methyl, ethyl, propyl, isopropyl, butyl, isobutyl, tert-butyl, pentyl, hexyl and the other isomeric forms thereof. ($C_1$-$C_3$)alkyl more specifically means methyl, ethyl, propyl, or isopropyl.

The term "alkenyl" refers to an alkyl group defined hereinabove having at least one unsaturated ethylene bond and the term "alkynyl" refers to an alkyl group defined hereinabove having at least one unsaturated acetylene bond. ($C_2$-$C_6$)alkylene includes a ethenyl, a propenyl (1-propenyl or 2-propenyl), a 1- or 2-methylpropenyl, a butenyl (1-butenyl, 2-butenyl, or 3-butenyl), a methylbutenyl, a 2-ethylpropenyl, a pentenyl (1-pentenyl, 2-pentenyl, 3-pentenyl, 4-pentenyl), an hexenyl (1-hexenyl, 2-hexenyl, 3-hexenyl, 4-hexenyl, 5-hexenyl), and the other isomeric forms thereof. ($C_2$-$C_6$)alkynyl includes ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl and the other isomeric forms thereof.

The term "epoxyalkyl" refers to an alkyl group defined hereinabove having an epoxide group. More particularly, ($C_2$-$C_6$)epoxyalkyl includes epoxyethyl, epoxypropyl, epoxybutyl, epoxypentyl, epoxyhexyl and the other isomeric forms thereof. ($C_2$-$C_3$)epoxyalkyl includes epoxyethyl and epoxypropyl.

The "aryl" groups are mono-, bi- or tri-cyclic aromatic hydrocarbons having from 6 to 18 carbon atoms. Examples include a phenyl, α-naphthyl, β-naphthyl or anthracenyl group, in particular.

"Heterocycle" groups are groups containing 5 to 18 rings comprising one or more heteroatoms, preferably 1 to 5 endocyclic heteroatoms. They may be mono-, bi- or tri-cyclic. They may be aromatic or not. Preferably, and more specifically for $R_5$, they are aromatic heterocycles. Examples of aromatic heterocycles include pyridine, pyridazine, pyrimidine, pyrazine, furan, thiophene, pyrrole, oxazole, thiazole, isothiazole, imidazole, pyrazole, oxadiazole, triazole, thiadiazole and triazine groups. Examples of bicycles include in particular quinoline, isoquinoline and quinazoline groups (for two 6-membered rings) and indole, benzimidazole, benzoxazole, benzothiazole and indazole (for a 6-membered ring and a 5-membered ring). Nonaromatic heterocycles comprise in particular piperazine, piperidine, etc.

"Alkoxy" groups correspond to the alkyl groups defined hereinabove bonded to the molecule by an —O— (ether) bond. ($C_1$-$C_6$)alkoxy includes methoxy, ethoxy, propyloxy, butyloxy, pentyloxy, hexyloxy and the other isomeric forms thereof. ($C_1$-$C_3$)alkoxy includes methoxy, ethoxy, propyloxy, and isopropyloxy.

"Alkyl" groups correspond to the alkyl groups defined hereinabove bonded to the molecule by an —CO— (carbonyl) group. ($C_2$-$C_6$)acyl includes acetyl, propylacyl, butylacyl, pentylacyl, hexylacyl and the other isomeric forms thereof. ($C_2$-$C_3$)acyl includes acetyl, propylacyl and isopropylacyl.

"Alcohol" groups correspond to the alkyl groups defined hereinabove containing at least one hydroxyl group. Alcohol can be primary, secondary or tertiary. ($C_1$-$C_6$)alcohol includes methanol, ethanol, propanol, butanol, pentanol, hexanol and the other isomeric forms thereof. ($C_1$-$C_3$)alcohol includes methanol, ethanol, propanol and isopropanol.

"Ester" groups correspond to the alkyl groups defined hereinabove bonded to the molecule by an —COO— (ester) bond. ($C_2$-$C_6$)ester includes methylester, ethylester, propylester, butylester, pentylester and the other isomeric forms thereof. ($C_2$-$C_3$)ester includes methylester and ethylester.

"Amine" groups correspond to the alkyl groups defined hereinabove bonded to the molecule by an —N— (amine) bond. ($C_1$-$C_6$)amine includes methylamine, ethylamine, propylamine, butylamine, pentylamine, hexylamine and the other isomeric forms thereof. ($C_1$-$C_3$)amine includes methylamine, ethylamine, and propylamine.

"Imine" groups correspond to the alkyl groups defined hereinabove having a (—C=N—) bond. ($C_1$-$C_6$)imine includes methylimine, ethylimine, propylimine, butylimine, pentylimine, hexylimine and the other isomeric forms thereof. ($C_1$-$C_3$)imine includes methylimine, ethylimine, and propylimine.

The halogen can be Cl, Br, I, or F, more preferably Br or F.

"Halogenoalkyl" groups correspond to the alkyl groups defined hereinabove having at least one halogen. The groups can be monohalogenated or polyhalogenated containing the same or different halogen atoms. For example, the group can be an trifluoroalkyl ($CF_3$—R). ($C_1$-$C_6$)halogenoalkyl includes halogenomethyl, halogenoethyl, halogenopropyl, halogenobutyl, halogenopentyl, halogenohexyl and the other isomeric forms thereof. ($C_1$-$C_3$)halogenoalkyl includes halogenomethyl, halogenoethyl, and halogenopropyl.

"Thioalkyl" groups correspond to the alkyl groups defined hereinabove bonded to the molecule by an —S— (thioether) bond. ($C_1$-$C_6$)thioalkyl includes thiomethyl, thioethyl, thiopropyl, thiobutyl, thiopentyl, thiohexyl and the other isomeric forms thereof. ($C_1$-$C_3$)thioalkyl includes thiomethyl, thioethyl, and thiopropyl.

"Sulfone" groups correspond to the alkyl groups defined hereinabove bonded to the molecule by an —SOO— (sulfone) bond. ($C_1$-$C_6$)sulfone includes methylsulfone, ethylsulfone, propylsulfone, butylsulfone, pentylsulfone, hexylsulfone and the other isomeric forms thereof. ($C_1$-$C_3$)sulfone includes methylsulfone, ethylsulfone and propylsulfone.

"Sulfoxyde" groups correspond to the alkyl groups defined hereinabove bonded to the molecule by an —SO— (sulfoxide) group. ($C_1$-$C_6$)sulfoxide includes methylsulfoxide, ethylsulfoxide, propylsulfoxide, butylsulfoxide, pentylsulfoxide, hexylsulfoxide and the other isomeric forms thereof. ($C_1$-$C_3$)sulfoxide includes methylsulfoxide, ethylsulfoxide, propylsulfoxide and isopropylsulfoxide.

"Heteroatom" denotes N, S, or O.

"Nucleoside" includes adenosine, thymine, uridine, cytidine and guanosine.

In a particular embodiment, the hydrocarbon group is a cycloalkylenyl such as a cyclopentadiene or a phenyl, or an heterocycle such as a furan, a pyrrole, a thiophene, a thiazole, an imidazole, a triazole, a pyridine, a pyrimidine, a pyrane, or a pyrazine. Preferably, the cycloalkylenyl or the heterocycle is selected from the group consisting of a cyclopentadiene, a pyrrole or an imidazole. In a preferred embodiment, the cycloalkylenyl or the heterocycle is substituted by an alcohol. Preferably, said alcohol is a ($C_1$-$C_3$)alcohol.

In an other embodiment, the hydrocarbon group is an alkylenyl with one or several double bonds. Preferably, the alkylenyl group has one double bond. Preferably, the alkylenyl group is a ($C_3$-$C_{10}$)alkylenyl group, more preferably a ($C_4$-$C_7$)alkylenyl group. Preferably, said alkylenyl group is substituted by at least one functional group. More preferably, the functional group is selected from the group consisting of an hydroxy, an ($C_1$-$C_3$)alkoxy, an aldehyde, an ($C_2$-$C_3$)acyl, or an ($C_2$-$C_3$)ester. In a more preferred embodiment, the hydrocarbon group is butenyl substituted by a group —$CH_2OH$. Optionally, said alkenyl group can be the isoform trans (E) or cis (Z), more preferably a trans isoform (Z). In one example, the alkylenyl group is (E or Z)-4-hydroxy-2-methylbut-2-enyl. In a particular embodiment, the compound is (E or Z) 5-hydroxy-3-methylpent-3-enyl pyrophosphonate or (E or Z) 4-hydroxy-2-methylbut-2-enyl pyrophosphoramidate.

In an additional embodiment, the hydrocarbon group is an alkyl group substituted by an acyl. More preferably, the hydrocarbon group is an ($C_4$-$C_7$)alkyl group substituted by an ($C_1$-$C_3$)acyl.

In a further particular preferred embodiment, R is selected from the group consisting of:

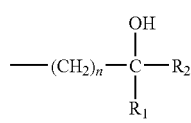

1)

wherein n is an integer from 2 to 20, $R_1$ is a ($C_1$-$C_3$)alkyl group, and $R_2$ is an halogenated ($C_1$-$C_3$)alkyl, a ($C_1$-$C_3$) alkoxy-($C_1$-$C_3$)alkyl, an halogenated ($C_2$-$C_3$)acyl or a ($C_1$-$C_3$)alkoxy-($C_2$-$C_3$)acyl. Preferably, $R_1$ is a methyl or ethyl group, and $R_2$ is an halogenated methyl (—$CH_2$—X, X being an halogen), an halogenated ($C_2$-$C_3$)acetyl, or ($C_1$-$C_3$) alkoxy-acetyl. The halogenated methyl or acetyl can be mono-, di-, or tri-halogenated. Preferably, n is an integer from 2 to 10, or from 2 to 5. In a more preferred embodiment, n is 2. In a most preferred embodiment, n is 2, $R_1$ is a methyl and $R_2$ is an halogenated methyl, more preferably a monohalogenated methyl, still more preferably a bromomethyl or iodomethyl. In a particularly preferred embodiment, n is 2, $R_1$ is a methyl, R2 is a bromomethyl. In a most preferred embodiment, R is 3-(bromomethyl)-3-butanol-1-yl.

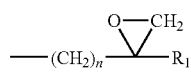

2)

wherein n is an integer from 2 to 20, and $R_1$ is a methyl or ethyl group. Preferably, n is an integer from 2 to 10, or from 2 to 5. In a more preferred embodiment, n is 2 and R1 is a methyl.

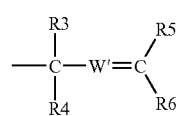

3)

wherein $R_3$, $R_4$, and $R_6$, identical or different, are a hydrogen or ($C_1$-$C_3$)alkyl group or any other isosteric group, W' is CH or N, and $R_5$ is an ($C_2$-$C_3$)acyl, an aldehyde, an ($C_1$-$C_3$) alcohol, or an ($C_2$-$C_3$)ester. More preferably, $R_6$ is a methyl and $R_3$ and $R_4$ are a hydrogen. Preferably, $R_5$ is —$CH_2$—OH, —CHO, —CO—$CH_3$ or —CO—$OCH_3$. More preferably, $R_5$ is —$CH_2$—OH. More preferably, W' is CH. Optionally, the double-bond between W and C is in conformation trans (E) or cis (Z). More preferably, the double-bond between W and C is in conformation trans (E).

The Y group can allow the design of a prodrug. Therefore, Y is enzymolabile group which can be cleaved in particular regions. The group Y can also be targeting group. In a preferred embodiment, Y is O⁻Cat+, a group -A-R, or a radical selected from the group consisting of a nucleoside, a monosaccharide, an epoxyde and a halohydrin. Preferably, Y is an enzymolabile group. Preferably, Y is O⁻Cat+, a group -A-R, or a nucleoside. In a first preferred embodiment, Y is O⁻Cat+. In a second preferred embodiment, Y is a nucleoside.

In a preferred embodiment, Cat+ is H+, Na+, $NH_4^+$, K+, Li+, ($CH_3CH_2$)$_3NH^+$, lysine, or any other suitable pharmaceutically acceptable cation.

In a preferred embodiment, A is O, NH, CHF, $CF_2$ or $CH_2$. Preferably, A is O, NH or $CH_2$. More preferably, A is O, or $CH_2$. Still more preferably, A is O.

In a preferred embodiment, B is O or NH. More preferably, B is O.

In a preferred embodiment, m is 1 or 2. More preferably, m is 1.

In a preferred embodiment, $R_3$, $R_6$ and $R_4$ are a hydrogen.

In a preferred embodiment, $R_5$ is —$CH_2$—OH, —CHO, —CO—$CH_3$ or —CO—$OCH_3$. More preferably, $R_5$ is —$CH_2$—OH.

In a preferred embodiment, $R_7$ is $CH_3$ or an isosteric group thereof, such as $CH_2F$, $CF_2H$ or $CF_3$. More preferably, $R_7$ is $CH_3$.

In a further aspect, said activator is a compound selected from the group consisting of:

A compound of Formula (II):

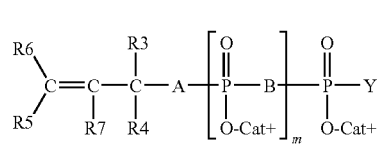

(II)

wherein Cat+ represents one (or several, identical or different) organic or mineral cation(s) (including proton);

m is an integer from 1 to 3;

B is O, NH, or any other group capable of being hydrolyzed;

A is O, NH, CHF, $CF_2$ or $CH_2$, or any other isosteric group;

$R_7$ is a ($C_1$-$C_3$)alkyl group or any other isosteric group such as $CF_3$;

$R_3$, $R_4$, and $R_6$, identical or different, are a hydrogen or a ($C_1$-$C_3$)alkyl group or any other isosteric group such as $CF_3$;

$R_5$ is an ($C_2$-$C_3$)acyl, an aldehyde, an ($C_1$-$C_3$)alcohol, or an ($C_2$-$C_3$)ester; and, Y is defined as in Formula (I).

Preferably, A is O or $CH_2$. More preferably, A is O. More preferably, $R_3$, $R_6$ and $R_4$ are a hydrogen. Preferably, $R_7$ is $CH_3$ or an isosteric group thereof. More preferably, $R_7$ is $CH_3$. Preferably, $R_5$ is —$CH_2$—OH, —CHO, —CO—$CH_3$ or —CO—$OCH_3$. More preferably, $R_5$ is —$CH_2$—OH. Preferably, Y is O⁻Cat+. Preferably, m is 1. Preferably, B is O In one embodiment, the group $R_5$ and the moiety —$CR_3R_4$-A-[POOB]$_m$—POOY of formula (II) are in E (or trans) configuration. In a preferred embodiment, the group $R_5$ and the moiety —$CR_3R_4$-A-[POOB]$_m$—POOY of formula (II) are in Z (or cis) configuration.

A compound of Formula (III):

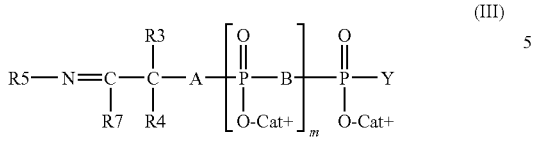

(III)

wherein Cat+ represents one (or several, identical or different) organic or mineral cation(s) (including proton);

m is an integer from 1 to 3;

B is O, NH, or any other group capable of being hydrolyzed;

A is O, NH, CHF, $CF_2$ or $CH_2$, or any other isosteric group such as $CF_3$;

$R_7$ is a $(C_1-C_3)$alkyl group or any other isosteric group such as $CF_3$;

$R_3$, and $R_4$, identical or different, are a hydrogen or a $(C_1-C_3)$alkyl group or any other isosteric group such as $CF_3$;

$R_5$ is an $(C_2-C_3)$acyl, an aldehyde, an $(C_1-C_3)$alcohol, or an $(C_2-C_3)$ester; and, Y is defined as in Formula (I).

Preferably, A is O or $CH_2$. More preferably, A is O. More preferably, $R_3$ and $R_4$ are a hydrogen. Preferably, $R_5$ is —$CH_2$—OH, —CHO, —CO—$CH_3$ or —CO—$OCH_3$. More preferably, $R_5$ is —$CH_2$—OH. Preferably, Y is O⁻Cat+. Preferably, m is 1. Preferably, B is O. Preferably, $R_7$ is $CH_3$ or an isosteric group thereof, such as $CH_2F$, $CF_2H$ or $CF_3$. More preferably, $R_7$ is $CH_3$. In one embodiment, the group $R_5$ and the moiety —$CR_3R_4$-A-[POOB]$_m$—POOY of formula (III) are in E (or trans) configuration. In a preferred embodiment, the group $R_5$ and the moiety —$CR_3R_4$-A-[POOB]$_m$—POOY of formula (III) are in Z (or cis) configuration.

A compound of Formula (IV):

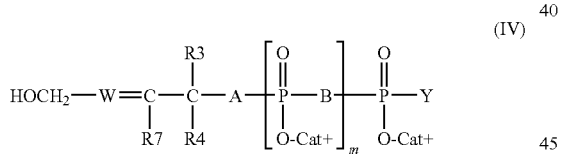

(IV)

wherein Cat+ represents one (or several, identical or different) organic or mineral cation(s) (including proton);

m is an integer from 1 to 3,

B is O, NH, or any other group capable of being hydrolysed,

A is O, NH, CHF, $CF_2$ or $CH_2$, and,

W is C—$R_6$ or N;

$R_7$ is a $(C_1-C_3)$allyl group or any other isosteric group such as $CF_3$, $R_3$, $R_4$, and $R_6$, identical or different, are a hydrogen or a $(C_1-C_3)$alkyl group or any other isosteric group, and Y is defined as in Formula (I).

Preferably, A is O or $CH_2$. More preferably, A is O. More preferably, $R_3$, $R_6$ and $R_4$ are a hydrogen. Preferably, $R_7$ is $CH_3$ or an isosteric group thereof. More preferably, $R_7$ is $CH_3$. Preferably, Y is O⁻Cat+. Preferably, m is 1. Preferably, B is O. In one embodiment, the group —$CH_2$—OH and the moiety —$CR_3R_4$-A-[POOB]$_m$—POOY of formula (IV) are in E (or trans) configuration. In a preferred embodiment, the group —$CH_2$—OH and the moiety —$CR_3R_4$-A-[POOB]$_m$—POOY of formula (IV) are in Z (or cis) configuration.

A compound of Formula (V):

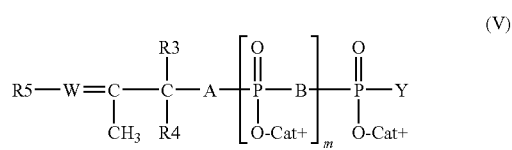

(V)

wherein Cat+ represents one (or several, identical or different) organic or mineral cation(s) (including proton);

m is an integer from 1 to 3,

B is O, NH, or any other group capable of being hydrolysed,

A is O, NH, CHF, $CF_2$ or $CH_2$,

W is C—$R_6$ or N;

$R_3$, $R_4$, and $R_6$, identical or different, are a hydrogen or $(C_1-C_3)$alkyl group or an isosteric group, $R_5$ is an $(C_2-C_3)$acyl, an aldehyde, an $(C_1-C_3)$alcohol, or an $(C_2-C_3)$ester, and Y is defined as in Formula (I).

Preferably, A is O or $CH_2$. More preferably, A is O. More preferably, $R_3$, $R_6$ and $R_4$ are a hydrogen. Preferably, $R_5$ is —$CH_2$—OH, —CHO, —CO—$CH_3$ or —CO—$OCH_3$. More preferably, $R_5$ is —$CH_2$—OH. Preferably, Y is O⁻Cat+. Preferably, m is 1. Preferably, B is O. In one embodiment, the compound of formula (V) is in E (or trans) configuration. In a preferred embodiment, the group compound of formula (V) is in Z (or cis) configuration.

A compound of Formula (VI):

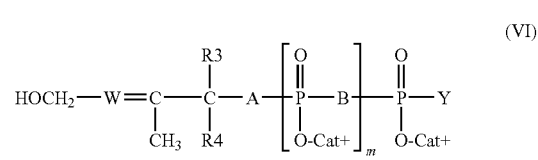

(VI)

wherein Cat+ represents one (or several, identical or different) organic or mineral cation(s) (including proton);

m is an integer from 1 to 3,

B is O, NH, or any other group capable of being hydrolysed,

A is O, NH, CHF, $CF_2$ or $CH_2$; and,

W is C—$R_6$ or N;

$R_3$, $R_4$, and $R_6$, identical or different, are a hydrogen or $(C_1-C_3)$alkyl group or an isosteric group, Y is defined as in Formula (I).

Preferably, A is O or $CH_2$. More preferably, A is O. More preferably, $R_3$, $R_6$ and $R_4$ are a hydrogen. Preferably, Y is O⁻Cat+. Preferably, m is 1. Preferably, B is O. In one embodiment, the compound of formula (VI) is in E (or trans) configuration. In a preferred embodiment, the compound of formula (VI) is in Z (or cis) configuration.

A compound of Formula (VII):

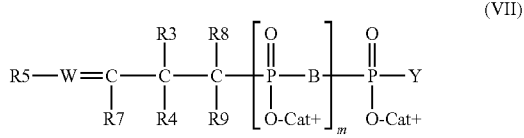

(VII)

wherein Cat+ represents one (or several, identical or different) organic or mineral cation(s) (including proton);
m is an integer from 1 to 3,
B is O, NH, or any other group capable of being hydrolysed,
W is C—$R_6$ or N;
$R_7$ is a ($C_1$-$C_3$)alkyl group or an isosteric group such as $CF_3$,
$R_3$, $R_4$, and $R_6$, identical or different, are a hydrogen or a ($C_1$-$C_3$)alkyl group or an isosteric group such as $CF_3$,
$R_8$ is H or F,
$R_9$ is H or F,
Y is defined as in Formula (I), and
$R_5$ is an ($C_2$-$C_3$)acyl, an aldehyde, an ($C_1$-$C_3$)alcohol, or an ($C_2$-$C_3$)ester.

Preferably, $R_3$, $R_6$ and $R_4$ are a hydrogen. Preferably, $R_5$ is —$CH_2$—OH, —CHO, —CO—$CH_3$ or —CO—$OCH_3$, more preferably —$CH_2$—OH. Preferably, $R_7$ is $CH_3$ or an isosteric group thereof, more preferably $CH_3$. Preferably, Y is $O^-Cat+$. Preferably, m is 1. Preferably, B is O. Preferably, $R_8$ and $R_9$ are a hydrogen. In one embodiment, the group $R_5$ and the moiety —$CR_3R_4$-A-$[POOB]_m$—POOY of formula (VII) are in E (or trans) configuration. In a preferred embodiment, the group $R_5$ and the moiety —$CR_3R_4$-A-$[POOB]_m$—POOY of formula (VII) are in Z (or cis) configuration.

A compound of Formula (VIII):

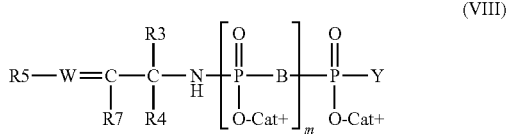

(VIII)

wherein Cat+ represents one (or several, identical or different) organic or mineral cation(s) (including proton);
m is an integer from 1 to 3,
B is O, NH, or any other group capable of being hydrolysed,
W is C—$R_6$ or N;
$R_7$ is a ($C_1$-$C_3$)alkyl group or an isosteric group such as $CF_3$,
$R_3$, $R_4$, and $R_6$, identical or different, are a hydrogen or a ($C_1$-$C_3$)alkyl group or an isosteric group such as $CF_3$,
Y is defined as in Formula (I), and
$R_5$ is an ($C_2$-$C_3$)acyl, an aldehyde, an ($C_1$-$C_3$)alcohol, or an ($C_2$-$C_3$)ester.

Preferably, $R_3$, $R_6$ and $R_4$ are a hydrogen. Preferably, $R_5$ is —$CH_2$—OH, —CHO, —CO—$CH_3$ or —CO—$OCH_3$, more preferably —$CH_2$—OH. Preferably, $R_7$ is $CH_3$ or an isosteric group thereof, more preferably $CH_3$. Preferably, Y is $O^-Cat+$. Preferably, m is 1. Preferably, B is O. In one embodiment, the group $R_5$ and the moiety —$CR_3R_4$-A-$[POOB]_m$—POOY of formula (VII) are in E (or trans) configuration. In a preferred embodiment, the group $R_5$ and the moiety —$CR_3R_4$-A-$[POOB]_m$—POOY of formula (VIII) are in Z (or cis) configuration.

A compound of Formula (IX):

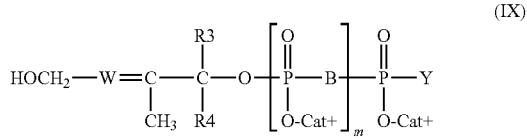

(IX)

wherein Cat+ represents one (or several, identical or different) organic or mineral cation(s) (including proton);
m is an integer from 1 to 3,
B is O, NH, or any other group capable of being hydrolysed,
W is C—$R_6$ or N;
$R_3$, $R_4$, and $R_6$, identical or different, are a hydrogen, an ($C_1$-$C_3$)alkyl group or an isosteric group such as $CF_3$,
Y is defined as in Formula (I).

Preferably, $R_3$, $R_6$ and $R_4$ are a hydrogen. Preferably, Y is $O^-Cat+$. Preferably, m is 1. Preferably, B is O. In one embodiment, the compound of formula (IX) is in E (or trans) configuration. In a preferred embodiment, the compound of formula (IX) is in Z (or cis) configuration.

A compound of Formula (X):

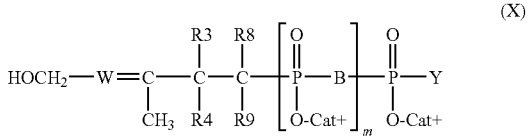

(X)

wherein Cat+ represents one (or several, identical or different) organic or mineral cation(s) (including proton);
m is an integer from 1 to 3,
B is O, NH, or any other group capable of being hydrolysed,
W is C—$R_6$ or N;
$R_3$, $R_4$, and $R_6$, identical or different, are a hydrogen, an ($C_1$-$C_3$)alkyl group or an isosteric group such as $CF_3$,
$R_8$ is H or F,
$R_9$ is H or F, and
Y is defined as in Formula (I).

Preferably, $R_3$, $R_6$ and $R_4$ are a hydrogen. Preferably, Y is $O^-Cat+$. Preferably, m is 1. Preferably, B is O. Preferably, $R_8$ and $R_9$ are a hydrogen. In one embodiment, the compound of formula (X) is in E (or trans) configuration. In a preferred embodiment, the compound of formula (X) is in Z (or cis) configuration.

A compound of formula (XI):

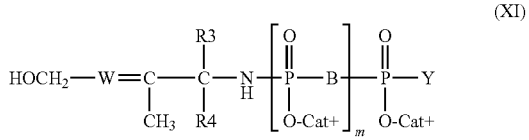

(XI)

wherein Cat+ represents one (or several, identical or different) organic or mineral cation(s) (including proton);
m is an integer from 1 to 3,
B is O, NH, or any other group capable of being hydrolysed,
W is C—$R_6$ or N;
$R_3$, $R_4$, and $R_6$, identical or different, are a hydrogen, an ($C_1$-$C_3$)alkyl group or an isosteric group such as $CF_3$, and
Y is defined as in Formula (I).

Preferably, $R_3$, $R_6$ and $R_4$ are a hydrogen. Preferably, Y is $O^-Cat+$. Preferably, m is 1. Preferably, B is O. In one embodiment, the compound of formula (XI) is in E (or trans) configuration. In a preferred embodiment, the compound of formula (XI) is in Z (or cis) configuration.

In further embodiments, the γδ T cell activator is a compound of formula (XII) or (XII'):

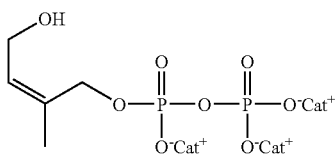

(XII)

(Z)-4-hydroxy-2-methylbut-2-enyl pyrophosphate (also referred to as HAngelylPP)

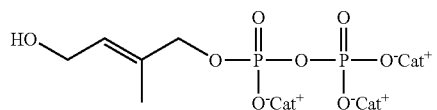

(XII')

(E)-4-hydroxy-2-methylbut-2-enyl pyrophosphate (also referred to as HTiglylPP)

In further embodiments, the γδ T cell activator is a compound of formula (XIII) or (XIII'):

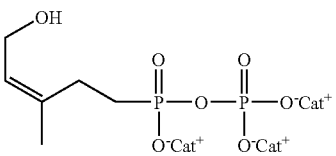

(XIII)

(Z)-5-hydroxy-3-methylpent-3-enyl pyrophosphonate (also referred to as C-HAngelylPP)

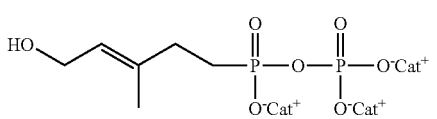

(XIII')

(E)-5-hydroxy-3-methylpent-3-enyl pyrophosphonate (also referred to as C-HTiglylPP)

In further embodiments, the γδ T cell activator is a compound of formula (XIV) or (XIV'):

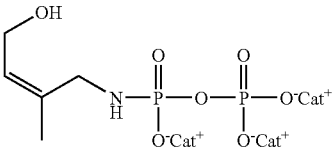

(XIV)

(Z)-4-hydroxy-2-methylbut-2-enyl pyrophosphoramidate (also referred to as N-HAngelylPP)

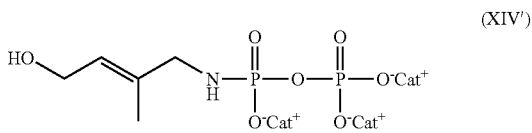

(XIV')

(E)-4-hydroxy-2-methylbut-2-enyl pyrophosphoramidate (also referred to as N-HTiglylPP)

In further embodiments, the γδ T cell activator is a compound of formula (XV):

(XV)

wherein Cat+ and A are defined as in Formula (I); X is H and Z is $CH_3$ (deoxyribonucleoside is thymydine) or X is OH and Z is H (ribonucleoside is uridine)

In one embodiment, the compound of formula (XV) is in E (or trans) configuration. In a preferred embodiment, the compound of formula (XV) is in Z (or cis) configuration.

Synthesis

As a general principle for exemplary methods, an alkyl moiety is prepared in a first step and coupled to a phosphorous containing moiety. For the sake of simplicity, the following schemes are shown for compounds where Y is O–Cat+. If a different Y group is desired, this can be prepared in a further step as described herein.

Depending on the type and reactivity of the functional groups provided by the alkyl moiety (represented by R in the discussion below), the person of skill in the art is able to adapt synthesis examples presented herein if necessary including the phases of protection/deprotection of the sensitive functional groups or those that can interact with the coupling reaction.

The coupling step is generally the critical step for synthesis and purification. A number of examples for coupling are provided as follows, depending on the identity of at position A.

Phosphate monoesters of Formula I or II, where A is O and where Y is O–Cat+, can be prepared using a coupling step according to conditions similar to those described in any of the publications: Davisson et al. (1984) and Davisson et al. (1987) and U.S. Pat. No. 6,660,723 to Belmant et al., the disclosures of each of which are incorporated herein by reference.

Phosphoramidate monoesters of Formula I or II, where A is NH and where Y is O–Cat+, can be prepared using a coupling step according to conditions similar to those described in any of the publications: Cox et al. (2002) and Sato et al. (1990) and copending PCT patent application nos. PCT/IB2004/

004311 and 60/579,237 to Belmant et al., the disclosures of each of which are incorporated herein by reference.

Phosphonate monoesters of Formula I or II, where A is CH2 and where Y is O–Cat+, can be prepared using a coupling step according to conditions similar to those described in publications: Valentijn (1991); Cox et al (2002), U.S. provisional patent applications 60/629,069, 60/564,959 to Tiollier, and PCT patent publication no. WO 03/050128, the disclosures of each of which are incorporated herein by reference.

Difluoro- and monofluorophosphonate monoesters of Formula I or II, where A is CF or CF2 and where Y is O–Cat+, can be prepared using a coupling step according to conditions similar to those described in publications: Cox et al. (2002), Waschbusch et al. (1997) and Burton et al. (1989), the disclosures of each of which are incorporated herein by reference.

Angelyl phosphoesters can be purified by preparative reversed phase HPLC on C18 according to the method reported by Zhang & Poulter (1993), by preparative chromatography on silica gel using ammoniac isopropanol eluents according to the methods of International Patent publication no. WO 03/050128 filed 5 Dec. 2002 for compounds having a good chemical stability in basic medium (phosphonate and angelyl phosphoesteres), or by chromatography on cellulose Davisson et al. (1984). The disclosures of the above references are incorporated herein by reference.

Compounds comprising a nucleoside as Y group can be prepared, for example, by the following reactions, Reaction A R—A—PP $\xrightarrow{\text{Nucl-O—V, acetonitrile}}$ R—A—PP—O—Nucl or Reaction B R—A—PP $\xrightarrow{\text{Nucl-O—V, acetonitrile}}$ R—A—PPP—O—Nucl where —O—V is a good leaving group beginning with V chosen, for example, from among tosyle, mesyle, triflyle, brosyle or bromium, PP represents the pyrophosphate group, PPP represents the triphosphate group, R-A- has the above mentioned meaning and Nucl is a nucleoside. Preferably, Nucl-O—V is selected from the group consisting of: 5'-O-Tosyladenosine, 5'-O-Tosyluridine, 5'-O-Tosylcytidine, 5'-O-Tosylthymidine or 5'-O-Tosyl-2'-deoxyadenosine.

Depending on the type and reactivity of the functional groups provided by Y, the professional is able to adapt the following examples, if necessary including the phases of protection/non-protection of the sensitive functional groups or those that can interact with the coupling reaction.

For example, for the compound with R as shown below, the reaction procedure can be the following:

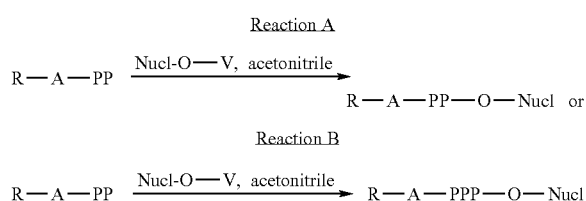

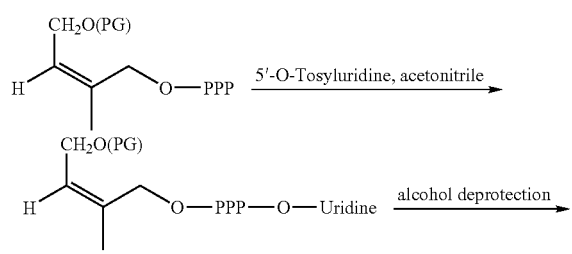

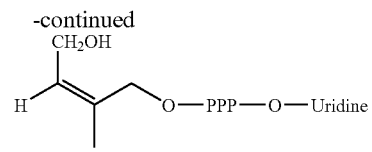

where PG represents a protective group of the alcohol function, and where —O—V is a good leaving group beginning with V chosen, for example, from among tosyle, mesyle, triflyle, brosyle or bromium, PP represents the pyrophosphate group and Nucl is a nucleoside. Preferably, Nucl-O—V is selected from the group consisting of: 5'-O-Tosyladenosine, 5'-O-Tosyluridine, 5'-O-Tosylcytidine, 5'-O-Tosylthymidine or 5'-O-Tosyl-2'-deoxyadenosine as described in Davisson et al, (1987), the disclosure of which is incorporated herein by reference.

Neutral pH is a nucleophile substitution reaction that can be carried out in conditions similar to those described by Davisson et al, (1987); and Davisson et al. (1986), the disclosures of which are incorporated herein by reference.

This reaction can also be used to prepare compound comprising a monosaccharide as group Y. In this case, Nucl-O—V is replaced by MonoSac-O—V, wherein Monosac is monosaccharide. For example, it is possible to use the MonoSac-O—Y group corresponding to compound Methyl-6-O-tosyl-alpha-D-galactopyranoside as described in publication Nilsson and Mosbach (1980), which disclosure is incorporated herein by reference, or the commercially available mannose triflate compound.

This reaction can further be used to prepare compound comprising a oligosaccharide as group Y. In this case, Nucl-O—V is replaced by oligoSac-O—V, wherein oligoSac is an oligosaccharide. For example, it is possible to use the oligoSac-O—Y group corresponding to compound $6^4$-O-p-Toluenesulfonyl-β-cyclodextrin as described in publication (Organic syntheses, Vol. 77, p 225-228, the disclosure of which is incorporated herein by reference).

This reaction can be used to prepare compound comprising a polysaccharide as group Y. In this case, Nucl-O—V is replaced by polySac-O—V, wherein polySac is a polysaccharide. For example, it is possible to use the polySac-O—Y group corresponding to tosylated polysaccharide as described in publication Nilsson et al., (1981); and Nilsson and Mosbach, (1980), the disclosures of which are incorporated herein by reference. This coupling technique based on the activation of the hydroxyl groups of a polysaccharide support by tosylation allows for covalent coupling in an aqueous or an organic medium.

This reaction can also be used for preparing compound comprising an aldehyde derivative as group Y by choosing, instead of Nucl, a derivative including a protected aldehyde function in the form of an acetal or any other group protecting this function.

Alternatively, compounds comprising a nucleoside as Y group can be prepared by the following reaction:

Reaction C

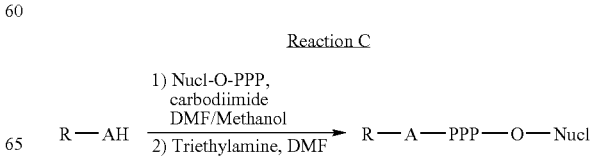

where PPP represents the triphosphate group, A is O or NH with R-AH representing a primary alcohol (R—OH) or a primary amine (R—NH$_2$), DMF is dimethylformamide, and Nucl is a nucleoside. This reaction can be carried out in conditions similar to those described by Knorre et al.(1976), or by Bloom et al., U.S. Pat. No. 5,639,653 (1997), the disclosures of which are incorporated herein by reference, from an alcohol and a nucleotide with formula Nucl-O-PPP.

For example, for the compound with R as shown below, the reaction procedure can be the following:

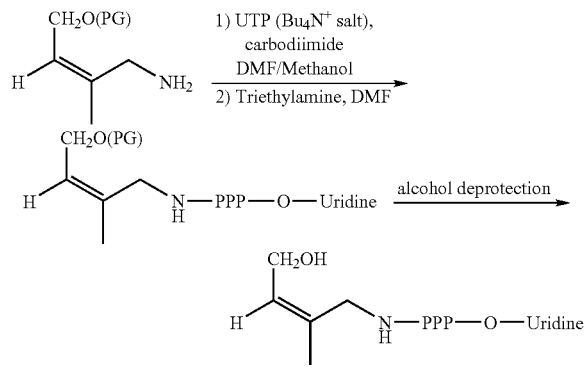

where PG represents a protective group of the alcohol function, UTP is Uridine Triphosphate, PPP represents the triphosphate group, DMF is dimethylformamide, and Nucl is a nucleoside.

This reaction can also be applied to the preparation of oligonucleotides 5'-triphosphate γ-esters as indicated by the authors of publication Knorre et al. (1976).

Compounds comprising a nucleic acid as Y group, more particularly a ribonucleic acid, can be prepared in conditions similar to those described in publication F. Huang et al (1997). The authors describe a universal method from catalytic RNA that is applicable to any molecule comprising a free terminal phosphate group. Compounds structurally related to the phosphohalohydrine group such as isopentenyl pyrophosphate or thiamine pyrophosphate are used or mentioned by these authors (see p. 8968 of F. Huang et al (1997)). It should also be noted that the experimental conditions for the coupling procedure (in particular pH conditions) described in the section eReaction of Isolate 6 pppRNA with phosphate containing Nucleophiles on page 8965 are compatible with the presence of a halohydrine function.

Compounds comprising an amino acid, a peptide or a protein derivative as Y group can be obtained using the well known reactivity of their primary amine or thiol function on an epoxyde function (S$_N$2 reaction). This type of coupling classically involves an intermediate group still called "linker" bearing an epoxyde function. An example of a reaction procedure using this type of coupling is provided by the following scheme, Reaction D

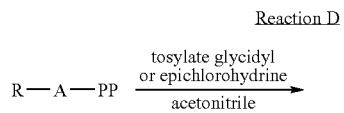

-continued

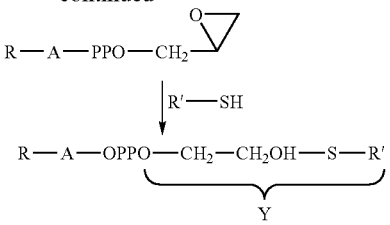

where PP represents the pyrophosphate group, R-A has the above mentioned meaning and R'—SH is an amino acid, a peptide or a protein derivative. The first phase can be carried out in conditions similar to those described by Davisson et al. (1987) and Davisson et al, (1986), the disclosures of which are incorporated herein by reference, from the tetrabutylammonium salt of the initial compound and commercially available compounds such as glycidyl tosylate or epichlorohydrine. This reaction can also be carried out with triphosphate compounds. Alternatively, a primary amine R'—NH$_2$ can be used instead of R'—SH. Without the reaction with R'—SH, the first reaction can be used to prepare compound comprising an epoxyde derivative.

Alternatively, compounds comprising an amino acid, a peptide or a protein derivative as Y group can be prepared by the following reaction:

Reaction E

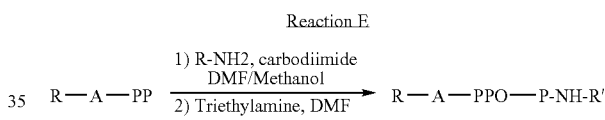

where PPP represents the triphosphate group, PP represents the pyrophosphate group, P represents the phosphate group, R-A has the above mentioned meaning and R'—NH is an amino acid, a peptide or a protein derivative. The reaction can be carried out in conditions similar to those described by Knorre et al. (1976), the disclosure of which is incorporated herein by reference, from compound (R-A-PPP) and an amino acid, peptide or a protein with formula R—NH$_2$. This reaction involves the protection of the sensitive functions of compound R—NH$_2$ or can react with the carbodiimide (in particular, the carboxyl function).

Tri or tetra-n-butylammonium salts of phosphoric, pyrophosphoric, triphosphoric, tetra-phosphoric or polyphosphoric acid can be prepared from commercially available corresponding acids. Derivatives with a related structure such as derivatives of methanetrisphosphonic acid described in publication Liu et al (1999), the disclosure of which is incorporated herein by reference, can also be prepared according to the reaction procedure.

The above mentioned reactions can be extrapolated to a very large spectrum of molecules or biomolecules by using the reactivity of the hydroxyl, amine, phosphate or thiol functions. Thereby, inositol derivatives can be prepared according to reactions A or B by activation of the hydroxyl function. Derivatives of folic acid (vitamin B9) or tetrahydrofolic acid can be prepared according to reactions D or E by calling on the reactivity of the primary amine function.

Of course, other types of coupling can be considered and the professional can have access to a large choice of reactions.

Thereby, coupling by phosphorylation of carboxylic acid or phenol groups can be used for the formation of fatty acid, lipid or certain flavonoid derivatives.

Assessing Activity of Compounds

The angelyl and tiglyl phosphoesters can be produced ex vivo or in vitro. They may be a purified or otherwise artificially produced (e.g., by chemical synthesis, or by microbiological process). The angelyl phosphoesters according to the present invention are preferably capable of activating Vγ9Vδ2 T lymphocytes. In a preferred embodiment, the compound is capable of selectively activating Vγ9Vδ2 T lymphocytes, indicating that the compound has a selective action towards specific cell populations, and essentially does not directly activate other T cell sub-types, such as Vδ1 T cells. Such selectivity, as disclosed in the present application, suggests that preferred compounds can cause a selective or targeted activation of the proliferation or biological activity of Vγ9Vδ2 T lymphocytes.

The angelyl phosphoesters preferably increases the biological activity or causes the proliferation of γδ T cells, preferably increasing the activation of γδ T cells, particularly increasing cytokine secretion from γδ T cells or increasing the cytolytic activity of γδ T cells, with or without also stimulating the proliferation or expansion of γδ T cells. Accordingly, the angelyl or tiglyl phosphoesters is administered in an amount and under conditions sufficient to increase the activity γδ T cells in a subject, preferably in an amount and under conditions sufficient to increase cytokine secretion by γδ T cells and/or to increase the cytolytic activity of γδ T cells. Cytokine secretion and cytolytic activity as well as γδ T cell proliferation can be assessed using any appropriate in vitro assay.

Most preferably the γδ T cells referred to in the present specification are Vγ9Vδ2 T cells, and preferably the angelyl and tiglyl phosphoesters regulate the activity of Vγ9Vδ2 T cells.

In one example, γδ T cell activation can be assessed by administering a compound to an individual (human or non-human primate) and assessing activation or proliferation of Vγ9Vδ2 T cell. In an exemplary protocol expansion of the Vγ9Vδ2 T cell population is assessed: an angelyl phosphoester is administered to a non-human primate such as a cynomolgus monkey by intravenous infusion (one administration by slow infusion, 50 ml over 30 minutes) in combination with IL-2 (0.9 million units twice daily by subcutaneous injection for 5 days); peripheral γδ lymphocytes are analysed by flow cytometry on total monkey blood, after double staining with anti-CD3-PE antibody and anti-Vgamma9-FITC antibodies and/or anti Vd2 antibodies, and cells are counted by flow cytometry. Peak expansion of the Vγ9Vδ2 T cell population is observed between days 3 and 8, generally at about days 4-6 after administration of an angelyl phosphoester.

Any other suitable tests can be used to assess cell proliferation. Assessment of proliferation or peripheral γδ lymphocytes can generally be analyzed by flow cytometry on total blood (for example total blood obtained from a monkey), after double staining with anti-CD3-PE antibody and anti-Vgamma9-FITC antibodies and/or anti Vd2 antibodies (CD3-PE: SP34 clone, BD Biosciences Pharmingen, Le Pont de Claix, France). Anti Vgamma 9, clone 7B6 is a monoclonal raised to human Vgamma 9 but that cross-reacts with cynomolgus monkey cells. It is purified by affinity chromatography on protein A and coupled to FITC. 50 μl monkey blood is incubated 15 min at RT with 5 μl anti-CD3-PE and 6 μl anti-delta2-FITC or 10 μl anti-gamma9-FITC antibodies. Antibodies are washed with 3 ml 1×PBS, centrifuged for 4 min at 1300 rpm at RT and supernatant is discarded. Red cells are lysed with the OptiLyse C reagent (Immunotech-Beckman-Coulter, Marseilles, France) according to the manufacturer's instructions. At the final step, stained white blood cells are recovered by centrifugation and resuspended in 300 μl PBS+0.2% PFA. Immediately before analysis, 50 μl calibrated Flow Count™ Fluorospheres (Immunotech-Beckman-Coulter, Marseilles, France) are added to the cells for absolute number counting of the populations of interest.

Preferably an angelyl phosphoester is capable of regulating the activity of a γδ T cell in a population of γδT cell clones in culture. The angelyl phosphoester is more preferably capable of regulating the activity of a γδ. T cell population of γδT cell clones in culture at millimolar concentration, preferably when the angelyl phosphoester is present in culture at a concentration of less than 100 mM. In one example, cytokine production or release is assessed. Vg9Vd2 cells are known producers of TNFα and IFNγ in vitro upon administration of the angelyl phosphoester. Shortly after angelyl phosphoester treatment, samples of sera are collected from an individual and are assayed by ELISA specific for TNFα or IFNγ.

Regulating the activity of a γδ. T cell can be assessed by any suitable means, preferably by assessing cytokine secretion, most preferably TNF-α secretion as described herein. Methods for obtaining a population of pure γδ T cell clones is described in Davodeau et al, (1993) and Moreau et al, (1986), the disclosures of which are incorporated herein by reference.

In any exemplary assay, cytokine secretion can be determined according to the methods described in Espinosa et al. (2001a), describing measurement of TNF-α release in a bioassay using TNF-α-sensitive cells. Briefly, $10^4$ γδT cells/well were incubated with stimulus plus 25 units of IL2/well in 100 μl of culture medium during 24 h at 37° C. Then, 50 μl of supernatant were added to 50 μl of WEHI cells plated at $3 \times 10^4$ cells/well in culture medium plus actinomycin D (2 μg/ml) and LiCl (40 mM) and incubated for 20 h at 37° C. Viability of the TNF-α-sensitive cells and measured with a 3-(4,5-dimethylthiazol-2-yl)-2,5-diphenyltetrazolium bromide assay. 50 μl of 3-(4,5-dimethylthiazol-2-yl)-2,5-diphenyltetrazolium bromide (Sigma; 2.5 mg/ml in phosphate-buffered saline) per well were added, and after 4 h of incubation at 37° C., 50 μl of solubilization buffer (20% SDS, 66% dimethyl formamide, pH 4.7) were added, and absorbance (570 nm) was measured. Levels of TNF-α release were then calculated from a standard curve obtained using purified human rTNF-α (PeproTech, Inc., Rocky Hill, N.J.). Interferon-γ released by activated T cells was measured by a sandwich enzyme-linked immunosorbent assay. $5 \times 10^4$ γδT cells/well were incubated with stimulus plus 25 units of IL2/well in 100 μl of culture medium during 24 h at 37° C. Then, 50 μl of supernatant were harvested for enzyme-linked immunosorbent assay using mouse monoclonal antibodies (BIOSOURCE, Camarillo, Calif.).

A preferred assay for cytolytic activity is a $^{51}Cr$ release assay. In exemplary assays, the cytolytic activity of γδ T cells is measured against autologous normal and tumor target cell lines, or control sensitive target cell lines such as Daudi and control resistant target cell line such as Raji in 4 h $^{51}Cr$ release assay. In a specific example, target cells were used in amounts of $2 \times 10^3$ cells/well and labeled with 100 μCi $^{51}Cr$ for 60 minutes. Effector/Target (E/T) ratio ranged from 30:1 to 3.75:1. Specific lysis (expressed as percentage) is calculated using the standard formula [(experimental-spontaneous release/total-spontaneous release)×100].

Use of Phosphoester According to the Present Invention

The invention concerns a pharmaceutical composition comprising an angelyl or tiglyl phosphoester according to the present invention. More particularly, said pharmaceutical composition comprises a therapeutically effective amount of an angelyl or tiglyl phosphoester, optionally together with a pharmaceutically acceptable carrier. The present invention concerns an angelyl or tiglyl phosphoester according to the present invention as a medicament. Also encompassed by the invention is the use of an angelyl or tiglyl phosphoester according to the present invention for the manufacture of a pharmaceutical preparation, preferably for the treatment of a cancer, an infectious disease, an autoimmune disease or an allergic disease.

In one aspect, the invention discloses a method for regulating the activity of $\gamma\delta$ T cells in a human subject, said method comprising the step of administering, in at least one treatment, a therapeutically effective amount of an angelyl or tiglyl phosphoester according to the present invention, optionally together with a pharmaceutically acceptable carrier. More particularly, said method activates of stimulates an activity of $\gamma\delta$ T cells in a human subject.

In a particular embodiment, the amount of said angelyl or tiglyl phosphoester is sufficient to expand the $\gamma\delta$ T cell population in a subject to reach at least 10%, 15%, 20%, 30%, 40%, 50% or 60%, or between 30-90% of total circulating lymphocytes. In another embodiment, the amount of said angelyl or tiglyl phosphoester is sufficient to induce an at least 10-fold increase in the $\gamma\delta$ T cell population in a subject. Preferably, said $\gamma\delta$ T cell population is assessed between day 4 and day 8 following administration of said angelyl phosphoester, more preferably at day 5, 6 or 7 following administration of said angelyl phosphoester. Preferably, said $\gamma\delta$ T cell population is assessed by flow cytometry. Preferably, said $\gamma\delta$ T cells are V$\gamma$9/V$\delta$2 T cells.

In a preferred embodiment, the invention concerns a method for treating a cancer, an infectious disease, an autoimmune disease or an allergic disease in a subject, said method comprising the step of administering, in at least one treatment, a therapeutically effective amount of an angelyl or tiglyl phosphoester according to the present invention, optionally together with a pharmaceutically acceptable carrier.

In the above methods and uses, the subject is preferably a human subject, such as a subject having a cancer, an infectious disease, an autoimmune disease or an allergic disease. The invention is indeed suitable to treat all conditions caused by or associated with the presence of pathological cells which are sensitive to $\gamma\delta$ T cell lysis.

The invention is particularly suited to stimulate the anti-tumor immunity of a subject having a solid or hematopoietic tumor. Preferably, said tumor is selected from the group consisting of lung, colorectal, prostate, breast or epidermoid head or neck tumors. In a preferred aspect of the invention, said tumor is a renal cancer, preferably a metastatic renal cancer. Alternatively, said tumor is selected from the group consisting of a melanoma, ovarian cancer, pancreas cancer, neuroblastoma, head or neck cancer, bladder cancer, renal cancer, brain cancer and gastric cancer. In preferred embodiments, the compounds can be used for the treatment of cancer as described in International Patent Application number WO2004050096, the disclosure of which is incorporated herein by reference.

The invention is also suitable to stimulate an anti-viral immune response in a subject. For example the compound of the invention can be used for the treatment of an individual having an infection by a virus selected from HIV, CMV, EBV, Influenza virus, HPV, HCV and HBV.

The compounds of the invention are also suitable in methods of stimulating an immune response in a subject having an infection by a pathogen causing tuberculosis, malaria, tularemia, colibacillosis, etc.

The compounds of the invention are also suitable in methods of treating (e.g., for stimulating an immune response in) a subject having an autoimmune disease, such as diabetes, multiple sclerosis, rheumatoid arthritis, etc. or a subject having an allergic disease, including asthma, airway hyper-responsiveness, etc. In preferred embodiments the compounds are used in therapeutic indications and according to the teachings of International Patent publication number WO2000US0026684 filed on 28 Sep. 2000 by Gelfand, Born, Lahn, and Kanehiro; International Patent publication no. WO 00/00182, filed 24 Jun. 1999 by Jomaa; and International patent publication no WO2005/102385 by Tiollier, the disclosures of each of the references being incorporated herein by reference.

Preferably, dosage (single administration) of an angelyl phosphoester compound according to the present invention for treatment is between about 1 µg/kg and about 1.2 g/kg.

It will be appreciated that the above dosages related to a group of compounds, and that each particular compound may vary in optimal doses, as further described herein for exemplary compounds. Nevertheless, compounds are preferably administered in a dose sufficient to significantly increase the biological activity of $\gamma\delta$ T cells or to significantly increase the $\gamma\delta$ T cell population in a subject. Said dose is preferably administered to the human by intravenous (i.v.) administration during 2 to 180 min, preferably 2 to 120 min, more preferably during about 5 to about 60 min, or most preferably during about 30 min or during about 60 min.

In preferred exemplary compounds, a compound of Formula I to XVIII is administered in a dosage (single administration) between about 1 µg/kg and about 1.2 g/kg, preferably between about 10 µg/kg and about 1.2 g/kg, more preferably between about 20 µg/kg and about 100 mg/kg. Most preferably, dosage (single administration) for three-weekly or four-weekly treatment (treatment every three weeks or every third week) is between about 1 µg/kg and about 1.2 g/kg, preferably between about 10 µg/kg and about 20 mg/kg, more preferably between about 10 µg/kg and about 100 mg/kg. This dose is preferably administered to the human by intravenous (i.v.) administration during 2 to 180 min, preferably 2 to 120 min, more preferably during about 5 to about 60 min, or most preferably during about 30 min or during about 60 min.

The active ingredients may be administered through different routes, typically by injection or oral administration. Injection may be carried out into various tissues, such as by intravenous, intra-peritoneal, intra-arterial, intra-muscular, intra-dermic, subcutaneous, etc. Preferred administration routes for the activators are intravenous and intramuscular. Preferred administration routes for the cytokine are subcutaneous, intravenous and intra-muscular.

The invention provides a method of regulating the activity of $\gamma\delta$ T cells in a mammalian subject, the method comprising administering to a subject in need thereof an effective amount of an angelyl or tiglyl phosphoester according to a treatment cycle in which $\gamma\delta$ T cell activity, preferably the $\gamma\delta$ T cell rate (number of $\gamma\delta$ T cells), is allowed to return to substantially basal rate prior to a second administration of the compound. As further described herein, in preferred embodiments, at least about one week, but more preferably at least about two weeks, are required for a patient's $\gamma\delta$ T cell rate to return to substantially basal rate.

Cycles shorter than about 7 days may not permit suitable stimulation of γδ T cell activity. The course of a preferred cycle is an at least 1-weekly cycle, but more preferably at least a 2-weekly cycle (at least about 14 days), or more preferably at least 3-weekly or 4-weekly, though cycles anywhere between 2-weekly and 4-weekly are preferred. Also effective and contemplated are cycles of up to 8-weekly, for example 5-weekly, 6-weekly, 7-weekly or 8-weekly.

In one preferred embodiment, administration of the angelyl or tiglyl phosphoester occurs on the first day of a 2-weekly to 4-weekly cycle (that is, an about 14 to 28 day weeks repeating cycle). In a preferred embodiment, the angelyl phosphoester is administered only the first day of the 2-weekly to 4-weekly, or preferably 3 weekly, cycle.

As mentioned, a subject will preferably be treated for at least two cycles, or more preferably for at least three cycles. In other aspect, treatment may continue for a greater number of cycles, for example at least 4, 5, 6 or more cycles can be envisioned.

Optionally, an angelyl or tiglyl phosphoester according to the present invention can also be used in combination with a cytokine, particularly for the treatment of cancer. Preferably, said cytokine is the interleukin 2 (IL-2) (Proleukin™, Chiron, Emeryville Calif., USA) or any biologically active fragment, variant or analogue thereof, i.e., any fragment, variant or analogue capable of binding to an IL-2 receptor and of inducing activation of γδT cells in the method of this invention. In other embodiments, the cytokine is an interleukin 7 or an interleukin 15. Preferably, said angelyl or tiglyl phosphoester and said interleukin polypeptide are administered separately to the subject.

Therefore, the methods of the invention comprises further administering a cytokine. While the compounds of the invention may be used with or without further administration, in a preferred aspect a cytokine can be administered, wherein said cytokine is capable of increasing the expansion of a γδ T cell population treated with an angelyl or tiglyl phosphoester compound, preferably wherein the cytokine is capable of inducing an expansion of a γδ T cell population which is greater than the expansion resulting from administration of the angelyl or tiglyl phosphoester compound in the absence of said cytokine. A preferred cytokine is an interleukin-2 polypeptide.

A cytokine having γδ T cell proliferation inducing activity, most preferably the interleukin-2 polypeptide, is administered at low doses, typically over a period of time comprised between 1 and 10 days. The angelyl phosphoester is preferably administered in a single dose, and typically at the beginning of a cycle. Preferably, the interleukin-2 polypeptide is administered at a daily dose comprised between 0.2 and 2 MU per day, even more preferably between 0.2 and 1.5 MU, further preferably between 0.2 and 1 MU. The daily dose of cytokine, preferably an interleukin-2 polypeptide, is administered as a single injection or in two injections.

In preferred aspects, a cytokine, most preferably IL-2, is administered daily for up to about 10 days, preferably for a period of between about 3 and 10 days, or most preferably for about 7 days. Preferably, the administration of the cytokine begins on the same day (e.g. within 24 hours of) as administration of the γδ T cell activator. For example, in one aspect the cytokine is administered each day, while in other aspects the cytokine need not be administered on each day. When the cytokine is administered for about 7 to about 14 days, a 4-weekly treatment cycle is preferred. When the first component is administered for about 4 days, a 3-weekly day treatment cycle is preferred. In preferred embodiments, the compounds can be used according to any of the methods described in International Patent Application number WO2004050096, the disclosure of which is incorporated herein by reference.

The above methods and treatments may be used alone or in combination with other active agents or treatments. For instance, for the treatment of tumors, the invention may be used in combination with other anti-tumor agents or treatments, such as chemotherapy, radiotherapy or gene therapy.

The invention also relates to a product comprising an angelyl or tiglyl phosphoester according to the present invention and an interleukin-2 polypeptide, for separate use, for regulating the activity of γδ T cells in a mammalian subject.

The invention concerns a vaccinal composition comprising an angelyl or tiglyl phosphoester according to the present invention. The invention also concerns the use of an angelyl or tiglyl phosphoester according to the present invention as a vaccine adjuvant.

Accordingly, the present invention discloses methods and compositions for enhancing and/or augmenting the immune response against an antigen in a mammal, notably a human, involving the conjoint immunization of the mammal with (i) a composition comprising an antigen and (ii) an adjuvant comprising an angelyl or tiglyl phosphoester compound according to the present invention. Preferably said composition comprising an antigen comprises a killed, inactivated or attenuated pathogen, microorganism or parasite. In other aspect, said composition comprising an antigen preferably comprises an enriched or purified polypeptide, lipid, polysaccharide, glycoprotein, glycolipid or nucleic acid antigen. Preferably said composition comprises at least 1, 2, 3, 4, 5, 10 or 15 distinct antigens, for example at least 1, 2, 3, 4, 5, 10 or 15 distinct polypeptides, or nuclei acids encoding such polypeptides. In preferred embodiments, the compounds can be used as described in U.S. Provisional Patent Application No. 60/564,959, filed Apr. 26, 2004, the disclosure of which is incorporated herein by reference.

The adjuvant composition will comprise an effective amount of an angelyl or tiglyl phosphoester compound according to the present invention, said amount being an effective amount allowing the elicitation of a humoral response, elicitation of a cytotoxic T lymphocyte (CTL) response, or elicitation of both a humoral response and a CTL response of the adjuvant composition with respect to at least one antigen. Preferably the angelyl or tiglyl phosphoester compound according to the present invention, is present in an amount effective to produce a greater immunological effect in eliciting a humoral response, a cytotoxic T lymphocyte (CTL) response or both a humoral response and a CTL response when administered conjointly with an antigen than that immunological effect produced when said antigen is administered in the absence of the adjuvant.

The antigen component of the composition can be selected from virtually any antigen, antigenic determinant or hapten of medical or veterinary interest, and particularly for those antigens for which an increase in immunogenicity is desired.

Therefore, the present invention concerns the use of an angelyl or tiglyl phosphoester compound according to the present invention, more preferably the compounds of Formulas I to XV, as a vaccine adjuvant. The present invention further concerns a vaccine composition comprising an antigen or a combination of antigens, and an angelyl or tiglyl phosphoester compound according to the present invention, more preferably the compounds of Formulas I to XV. Preferably, said composition comprises a therapeutically effective amount of antigen and an immune response enhancing or immune response augmenting amount of the angelyl or tiglyl phosphoester. Preferably, said vaccine composition prevents a microbial infection. Said microbial infection is caused by a microbe selected from the group consisting of viruses, fungi, parasites, yeast, bacteria, and protozoa. In a particular embodiment, said vaccine composition is BCG vaccine composition. Alternatively, said vaccine composition prevents or is a treatment against a tumor.

The present invention further concerns a vaccine kit comprising a suitable container containing a vaccine composition according to the present invention, more particularly comprising an antigen or a combination of antigens, and an angelyl or tiglyl phosphoester compound according to the present invention, more preferably the compounds of Formulas I to XV. Optionally, said vaccine can comprise two separate suitable containers, one containing the antigen or the combination of antigens and the other containing an angelyl or tiglyl phosphoester compound according to the present invention, more preferably the compounds of Formulas I to XV. Optionally, said container can be a syringue. Alternatively, said vaccine kit comprises one or two containers and a syringue.

The present invention concerns a method of improving the potency of a vaccine in a subject, or of immunizing a subject against a disease, more particularly a microbial infection, comprising the steps of:
  administering to said subject a composition comprising an antigen or a combination of antigens; and,
  conjointly administering to said subject an angelyl or tiglyl phosphoester compound according to the present invention, more preferably the compounds of Formulas I to XV, more particularly an immune response enhancing amount thereof. Preferably, the angelyl or tiglyl phosphoester compound according to the present invention, when administered conjointly with a composition comprising an antigen, is administered in an amount sufficient to enhance an immune response over that observed with said composition comprising an antigen in the absence of the angelyl phosphoester. Preferably said composition comprising an antigen comprises a killed, inactivated or attenuated pathogen, microorganism or parasite. In other aspect, said composition comprising an antigen preferably comprises an enriched or purified polypeptide, lipid, polysaccharide, glycoprotein, glycolipid or nucleic acid antigen.

The present invention also concerns a method of immunizing a subject against a disease, more particularly a microbial infection, in a subject comprising administering to said subject (i) a composition comprising an antigen, and (ii) an angelyl or tiglyl phosphoester compound according to the present invention, more preferably Formulas I to XV. Preferably the angelyl or tiglyl phosphoester compound according to the present invention is administered in an immune response enhancing amount. Preferably the angelyl or tiglyl phosphoester and the composition comprising an antigen are administered as a single vaccine composition in a therapeutically effective amount.

Preferably, said angelyl or tiglyl phosphoester is provided or administered together with a pharmaceutically acceptable carrier. In a first aspect, said administrations of said antigen or combination of antigens and said angelyl or tiglyl phosphoester are simultaneously. In a second aspect, said administrations of said antigen or combination of antigens and said angelyl or tiglyl phosphoester are administered sequentially. More particularly, said angelyl or tiglyl phosphoester can be administered prior to, concurrently with or subsequent to administration of an antigen or a combination of antigens to a subject for immunization purposes. Preferably, said antigen or combination of antigens are microbial antigens, preferably, viral, bacterial, fungal, protozoan, yeast or parasite antigens.

In a preferred embodiment, said antigen is a antigen of *Mycobacterium bovis*. Optionally, said antigen or combination of antigens is a tumoral antigen.

Further aspects and advantages of this invention will be disclosed in the following examples, which should be regarded as illustrative and not limiting the scope of this application.

EXAMPLES

Example 1

Synthesis of (E)-4-hydroxy-2-methyl-but-2-enyl pyrophosphate (Hydroxytiglyl pyrophosphate or HTiglylPP)

The synthesis of HTiglylPP was carried out according to the scheme presented in FIG. 1 starting from commercially available 2-methyl-2-vinyloxirane.

Preparation of (E)-4-Chloro-2-methylbut-2-en-1-ol 16 ml (179 mmol) of $TiCl_4$ was added under nitrogen to 360 ml of $CH_2Cl_2$. The solution was cooled to 90° C. and a solution of 10.0 g (119 mmol) of 2-methyl-2-vinyloxirane in 50 ml of $CH_2Cl_2$ was added dropwise keeping the temperature below −80° C. The red solution was then stirred at 80° C. for 2 hours and quenched with 600 ml of 1M HCl. The organic phase was separated and the aqueous phase was extracted with 3×500 ml of $Et_2O$. The combined organic phases were dried over $MgSO_4$, filtered and evaporated at 350 mbar at 25° C. to give 12.02 g (99.7 mmol, 84% yield) of 4-Chloro-2-methylbut-2-en-1-ol as brownish oil. The crude product was directly used in the next step.

Preparation of (E)-2-(4-Chloro-2-methylbut-2-en yloxy)tetrahydro-2H-pyran

To a solution of 11.5 g (95.37 mmol) of 4-Chloro-2-methylbut-2-en-1-ol in 120 ml of $CH_2Cl_2$ was added 26 ml (286.11 mmol) of Dihydropyrane (DHP). The solution was cooled at 0° C. and 2.4 g (9.53 mmol) of pyridinium p-toluene sulfonate (PPTS) was added portion wise. The solution was stirred for 3 hours at 0° C. The organic phase was washed with 3×50 ml of water, dried over $Na_2SO_4$, filtered and concentrated to give the crude product. The product was then purified by chromatography on silica gel using heptane/EtOAc (9/1) as eluent. 12.35 g (60.33 mmol, 64% yield) of the protected allylic alcohol were isolated as colorless oil.

Preparation of (E)-3-methyl-4-(tetrahydro-2H-pyran-2-yloxy)but-2-enyl acetate

To a solution of 1.0 g (5 mmol) of the protected allylic alcohol (E)-2-(4-Chloro-2-methylbut-2-en yloxy)tetrahydro-2H-pyran in 30 ml of DMF was added 820 mg (10 mmol) of sodium acetate followed by a catalytic amount of NaI (20 mg). The reaction mixture was heated at 80° C. for 6 hours. The reaction mixture was cooled and poured onto 200 ml of water. The solution was extracted with 3×50 ml of EtOAc. The combined organic phases were dried over Na2SO4, filtered and concentrated to give the crude product. This product was then purified by chromatography on silica gel using Heptane/EtOAc (8/2) as eluent. 463 mg (2.03 mmol, 40%) of (E)-3-methyl-4-(tetrahydro-2H-pyran-2-yloxy)but-2-enyl acetate were isolated as colour less oil.

Preparation of (E)-4-bromo-3-methylbut-2-enyl acetate

To a solution of 460 mg (2.0 mmol) of (E)-3-methyl-4-(tetrahydro-2H-pyran-2-yloxy)but-2-enyl acetate in 20 ml of $CH_2Cl_2$ was added a solution of 1.33 g (4 mmol) of $CBr_4$ in 10 ml of $CH_2Cl_2$. The solution was cooled to 0° C. and a solution of 1.05 g (4 mmol) of triphenylphosphine was added dropwise. The solution was allowed to warm up to room temperature for 6 hours and stirred at the same temperature for further 1 hour. The precipitate was filtered and the filtrate was evaporated. The residue was purified by chromatography on silica gel using Heptane/EtOAc (8/2) as eluent. 314 mg (1.52 mmol, 76%) of (E)-4-bromo-3-methylbut-2-enyl acetate were isolated as colourless oil.

Preparation of (E)-4-hydroxy-2-methylbut-2-enyl pyrophosphate

A solution of 900 mg (4.35 mmol) of (E)-4-bromo-3-methylbut-2-enyl acetate in 10 ml of $CH_3CN$ was added dropwise to a solution of 5.9 g (6.52 mmol) of TTAPP in 15 ml of $CH_3CN$. The reaction mixture was stirred at room temperature overnight and the solvent was evaporated. The residue was then passed through Dowex 50WX8 ($NH_4^+$form) resin column and eluted with 2 volumes of 40 mM of $NH_4HCO_3$ aqueous solution. The fraction was evaporated under high vacuum at 40-45° C. The residue was stirred with 4-5 ml of iPrOH/$NH_4OH$ 28% (1/1) and the unsoluble solid was filtered off. The filtrate was chromatographied on silica gel using iPrOH/$NH_4OH$ 28% 1/1) as eluent. 197 mg (0.752 mmol, 17%) of (E)-4-hydroxy-2-methylbut-2-enyl pyrophosphate, ammonium salt were isolated as a white solid. Under these conditions, the deprotection of the acetate moiety (alcohol protecting group) took place while chromatography on silica gel. The isomeric ratio (E:Z) in the purified product was 96:4 on the basis of Ionic Chromatography (HPAEC) analysis.

Each E and Z stereoisomer of 4-hydroxy-2-methylbut-2-enyl pyrophosphate was obtained as a pure compound by chromatographic purification (HPAEC) through IonPac® AS11 column, with multiple chromatographic passes being combined.

For the purpose of performing biological testing, neutral aqueous solutions of the product was sterilized by filtration through 0.2 μm filter and stored at −20° C. In the case of testing performed in vivo the solutions are passed beforehand through a DOWEX 50WX8-200 cationic resin column ($Na^+$ form) eluted by two column volumes of deionized water.

Example 2

Synthesis of (Z)-4-hydroxy-2-methyl-but-2-enyl pyrophosphate (Hydroxyangelyl pyrophosphate or HAngelylPP)

Figure 2:
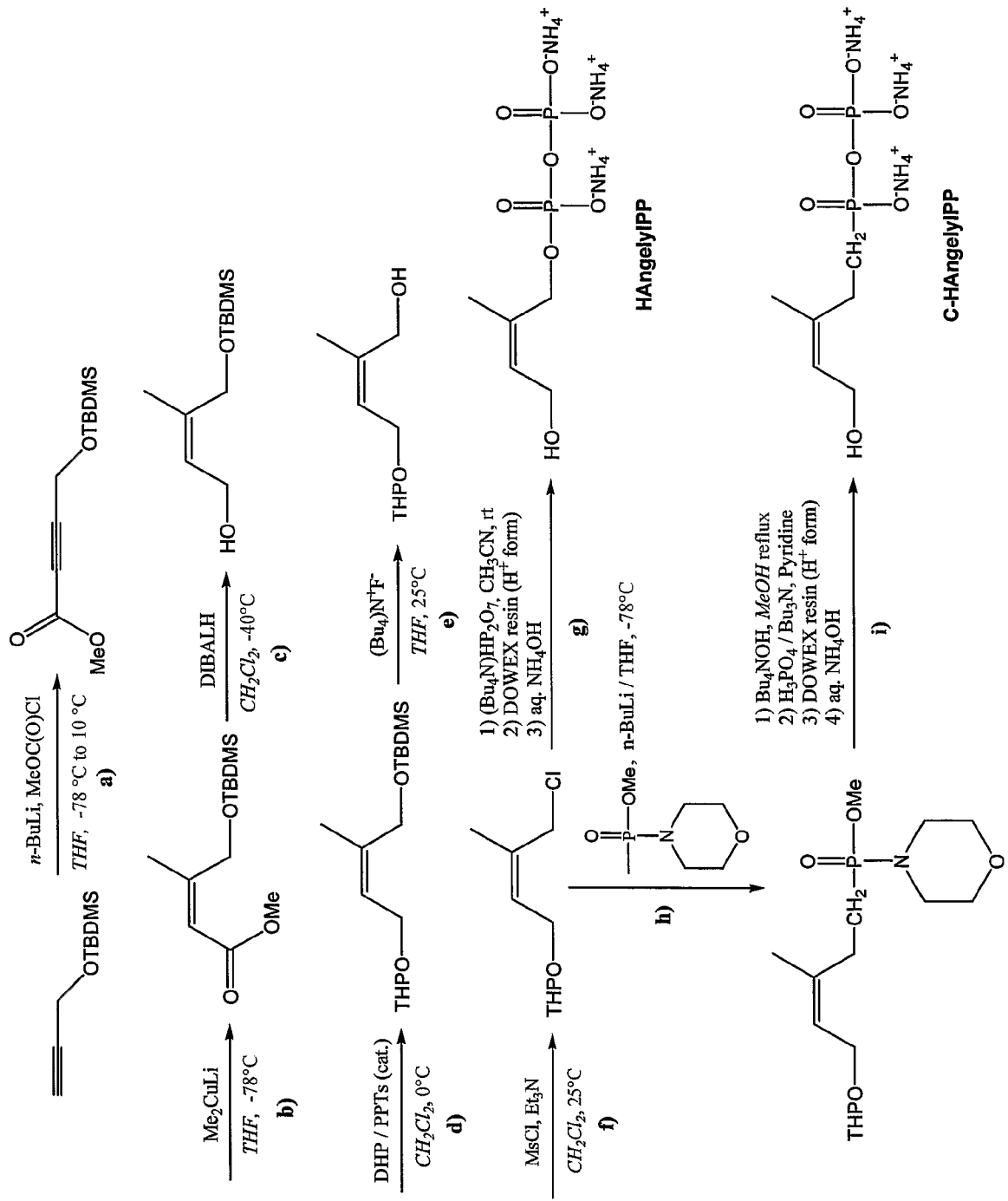
FIG. 2 is a synthetic scheme for the preparation of compounds H-AngelylPP and C-HAngelylPP as carried out in Examples 2 and 3.

The synthesis of (Z)-4-hydroxy-2-methylbut-2-enyl pyrophosphate (HAngelylPP) is carried out according to the scheme illustrated in FIG. 2 starting from commercially available TBDMS-protected propargyl alcohol. For each step of this synthetic scheme the following references may be used for further guidance:

Step a (propargyl ester formation from methyl chloroformate): Andrew T. Koppisch et al, *Organic Letters*, Vol. 2 No. 2 (2000) p 215-217; Michael S. Leonard and al, *J. Org. Chem.* (2004), 69, 2526-2531;

Step b (stereoselective conjugate addition of dimethylcopperlithium reagent to the α,β acetylenic ester): E. J. Corey and John A. Katzenellenbogen, J. Am. Chem. Soc. (1969), 91, 1851-1852; Andrew T. Koppissch et al, *Organic Letters*, Vol. 2 No. 2 (2000) p 215-217; Michael S. Leonard and al, *J. Org. Chem.* (2004), 69, 2526-2531;

Step c (ester reduction with DIBAL hydride): Andrew T. Koppisch et al, *Organic Letters*, Vol. 2 No. 2 (2000) p 215-217; Michael S. Leonard et al, *J. Org. Chem.* (2004), 69, 2526-2531;

Step d: the allylic alcohol is converted into a THP-protected form by reaction with dihydropyrane (DHP) following the procedure reported in example 1 or as described by Miyashita et al (Miyashita et al, *J. Org. Chem.* 42 (1977) 3772-3774);

Step e: (non acidic cleavage of the t-butyldimethylsilyl protective group): E. J. Corey and A. Venkateswarlu, J. Am. Chem. Soc. (1972), 94, 6190; alternative conditions for this deprotection reaction can also be found in "Protective Groups in Organic Synthesis", Third Edition, Theodora W. Greene and Peter G. M. Wuts, published by John Wiley & Sons, Inc. (1999);

Step f (chlorination step): in a standard procedure, triethylamine is added to a solution of the allylic alcohol in $CH_2Cl_2$ at 25° C. The resulting clear reaction mixture is then treated by the dropwise addition of mesyl chloride during 20 min. After complete addition, the reaction mixture is stirred at room temperature for at least 1.5 hours until complete conversion. The reaction mixture is washed successively with saturated aqueous $NaHCO_3$ solution, 0.1 M aqueous HCl and deionized water then concentrated under reduced pressure. The crude product is purified by chromatography using $SiO_2$ and an elution solvent of ethyl acetate:heptane=1:9;

Step g: the pyrophosphorylation of the THP-protected angelyl chloride with Tris tetra-n-butylammonium hydrogen diphosphate (TTAPP) is achieved following the general procedure reported by Poulter and co-workers (David T. Fox and C. Dale Poulter, *J. Org. Chem.* (2002), 67, 5009-5010; Davisson V. J. et al., J. Org. Chem., 1986, 51, p 4768-4779. Deprotection of the tetrahydropyranyl group is achieved by treatment of the pyrophosphate ester with DOWEX 50WX8 ($H^+$ form) cation exchange resin and subsequent neutralization of the resulting acidic solution with ammonium hydroxide.

For the purpose of performing biological testing, neutral aqueous solutions of the product is sterilized by filtration through 0.2 μm filter and stored at −20° C. In the case of testing performed in vivo the solutions are passed beforehand through a DOWEX 50WX8-200 cationic resin column ($Na^+$ form) eluted by two column volumes of deionized water.

Example 3

Synthesis of (Z)-5-hydroxy-3-methylpent-3-enyl pyrophosphonate (Hydroxyangelyl pyrophosphonate or C-HAngelylPP)

The synthesis of (Z)-5-hydroxy-3-methylpent-3-enyl pyrophosphonate (C-HAngelylPP) is performed according to the scheme illustrated in FIG. 2 from the THP-protected chloromethylbutenyl intermediate (product of step f) whose preparation is described in example 1.

Chemical reactions of step h and step i involving coupling of the pyrophosphonate moiety is carried out following the procedure of Valentijn et al for the preparation of Farnesyl Pyrophosphate analogues (Valentijn et al, *Synlett* (1991) 663-664):

Step i:
The phosphonylating agent (methyl methylphosphonomorpholidate) is prepared by treatment of commercially available methylphosphonic dichloride with morpholine and methanol. The coupling product is obtained by reaction of the THP-protected chloromethylbutenyl intermediate with methyl lithiomethylphosphonomorpholidate prepared in situ from the phosphonylating agent and n-butyl lithium in THF.

Step h:

A crude solution of C-HAngelylPP is obtained in a 3-step procedure:
1) Demethylation (hydrolysis) of the product of step i by treatment with tetra-n-butylammonium hydroxide in methanol as described by Phan and Poulter, J. Org. Chem. (2001), 66, 6705-6710,
2) Pyrophosphorylation with phosphoric acid (as tributy-lammonium salt) following the method of Valentijn et al,
3) Deprotection of the tetrahydropyranyl group by treatment of the pyrophosphonate ester with DOWEX 50WX8 ($H^+$ form) cation exchange resin and subsequent neutralization of the resulting acidic solution with ammonium hydroxide.

Purification of the resulting crude solution is performed by chromatography over silica gel using 25% ammonia solution/ 2-propanol 50/50 (v/v) as eluant. For the purpose of performing biological testing, the aqueous solutions of the product are sterilized by filtration through a 0.2 µm filter and stored at −20° C. In the case of testing performed in vivo, the solutions are passed beforehand through a DOWEX 50WX8-200 cationic resin column (sodium form) eluted by two column volumes of deionized water.

Example 4

Dosage Response for HAngelylPP and HtiglylPP Compounds

Cytokine Release Assay

Cells (primary polyclonal human Vγ9Vδ2 T cells which have been expanded in vitro and stored frozen at day 12-15 of expansion) are thawed and rinsed twice and centrifuged. Upon elimination of supernatant and resuspension of cells, the cells are incubated for 24 h at 37° C. in the presence of IL2 100 IU/ml (final concentration). The cells are washed and centrifuged, following which the supernatant is eliminated and the cells are resuspended and adjusted to the adequate final concentration. The cells are added to the wells of a 96-well plate.

To one row of wells is added a standard dilution series of (R,S)-3-(bromomethyl)-3-butanol-1-yl-diphosphate (R,S-BrHPP). Compounds to be tested, in this case (E)-4-hydroxy-3-methyl-2-butenyl pyrophosphate ((E)-HDMAPP) and the HAngelylPP and HTiglylPP compounds of the Angelyl/Tiglyl phosphoester series are added to experimental wells, after several dilutions.

Full plates are incubated 24 hours at 37° C. for stimulation of the γδ cells with the test compound and reference compounds, in this case HAngelylPP and HTiglylPP, (R,S)—BrHPP and (E) —HDMAPP, as further described below. After this time, 100 µl of culture supernatant is taken for TNFα dosage. Measurement of the released TNFα dosage is performed as described by the manufacturer's instruction in the TNFα enzyme immunoassay kit (ref. 11121, Immunotech—Beckman Coulter). OD at 405 nm is read, the OD being proportional to the concentration of released TNFα in the culture supernatant. The data are processed with the Excel software to compare concentration of test compound versus concentration of TNFα and for the calculation of the EC50 for each test compound.

HAngelylPP in vitro Bioactivity

Figure 3:
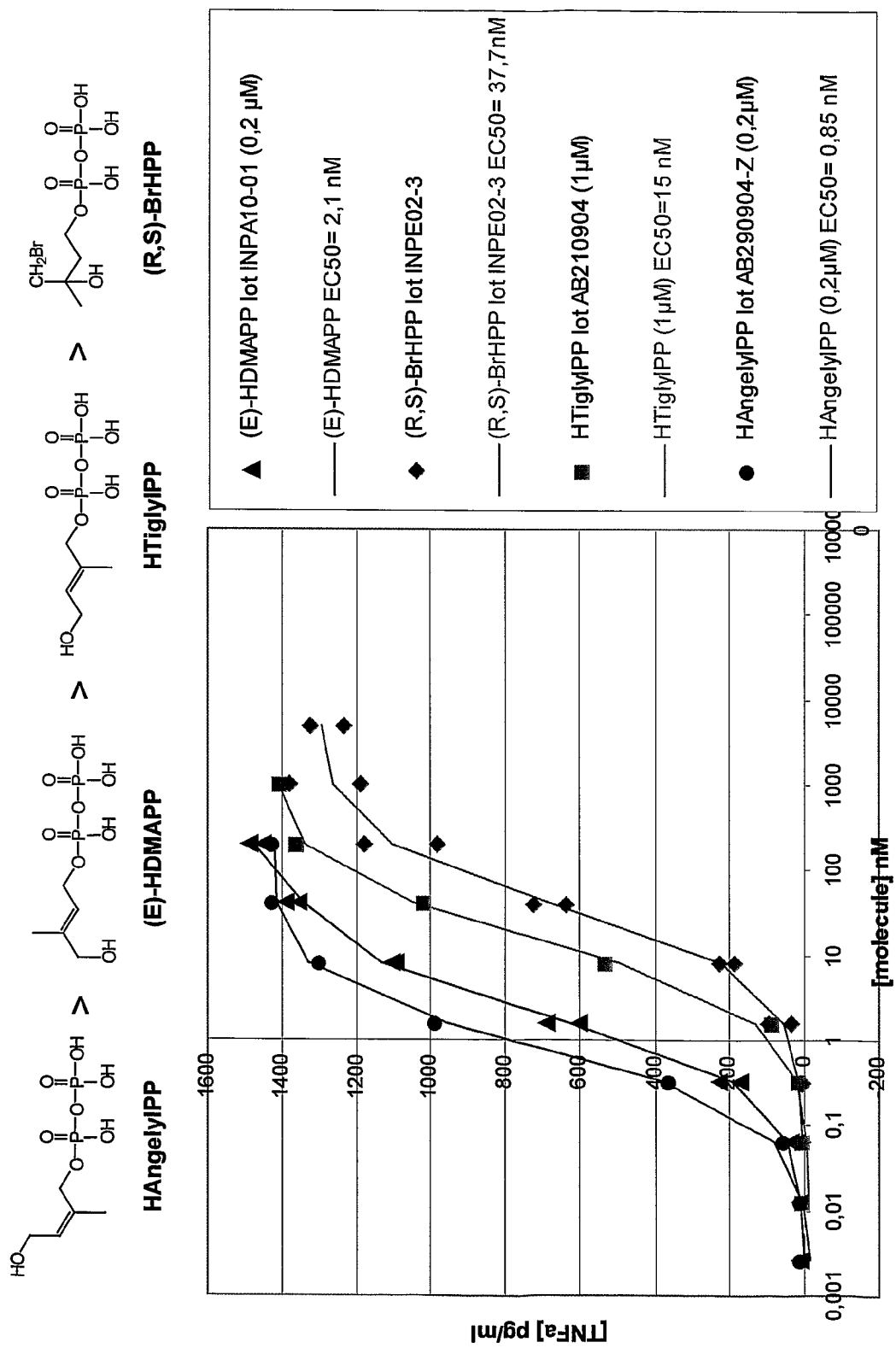
FIG. 3 shows an in vitro dose response curve and EC50 values for compounds of the invention HAngelylPP and HTiglylPP, and reference compounds (R,S)—BrHPP and (E)-HDMAPP.

The bioactivity of the compound HAngelylPP was assessed using a TNFα release assay as described above. In vitro activity is shown in FIG. 3. Compounds (R,S)—BrHPP and (E)-HDMAPP were included for purpose of comparison.

The in vitro EC50 was then assessed in this in vitro relative screening test, where prior assays with calibrated cells using a (R,S)-BrHPP-standard composition presented an EC50 of about 15 nM for the reference (R,S)-BrHPP compound. As will be appreciated, any other suitable assays such as cell amplification may be used in assessing compounds. The in vitro EC50 for HAngelylPP (Z isomer) was determined to be 0.85 mM and for HTiglylPP (E isomer) was 15 nM, while the in vitro EC50 for (E)-HDMAPP was 2.1 mM and the in vitro EC50 for (R,S)-BrHPP was 37.7 nM. Since the assay provides a relative result rather than absolute EC50 value, the results indicate that both HAngelylPP and HTiglylPP compounds are highly potent, and that the Z isomer (HAngelylPP) is the most potent compound of those tested.

REFERENCES

All the cited references are incorporated herein by reference.

Azzi, A., Casey, R. P. & Nalecz, M. (1984) The effect of N,N'-dicyclohexylcarbodiimide on enzymes of bioenergetic relevance. *Biochim. Biophys. Acta*, 768(3-4):209-226

Bank, I., Book, M., Huszar, M., Baram, Y., Schnirer, I., and Brenner, H. (1993). V delta 2+ gamma delta T lymphocytes are cytotoxic to the MCF 7 breast carcinoma cell line and can be detected among the T cells that infiltrate breast tumors. Clin Immunol Immunopathol 67, 17-24.

Behr, C., Poupot, R., Peyrat, M. A., Poquet, Y., Constant, P., Dubois, P., Bonneville, M., and Fournie, J. J. (1996). *Plasmodium falciparum* stimuli for human gammadelta T cells are related to phosphorylated antigens of mycobacteria. Infect Immun 64, 2892-2896.

Belmant, C., Espinosa, E., Halary, F., Tang, Y., Peyrat, M. A., Sicard, H., Kozikowski, A., Buelow, R., Poupot, R., Bonneville, M., and Fournie, J. J. (2000). A chemical basis for selective recognition of nonpeptide antigens by human delta T cells. Faseb J 14, 1669-1670.

Bukowski, J. F., Morita, C. T., Tanaka, Y., Bloom, B. R., Brenner, M. B., and Band, H. (1995). V gamma 2V delta 2 TCR-dependent recognition of non-peptide antigens and Daudi cells analyzed by TCR gene transfer. J Immunol 154, 998-1006.

Burton D. J., and Sprague, L. G. (1989). Allylations of [(Diethoxyphosphinyl)difluoromethyl]zinc Bromide as a convenient route of 1,1-Difluoro-3-alkenephosphonates. J. Org. Chem. 54, 613-617. Choudhary, A., Davodeau, F., Moreau, A., Peyrat, M. A., Bonneville, M., and Jotereau, F. (1995). Selective lysis of autologous tumor cells by recurrent gamma delta tumor-infiltrating lymphocytes from renal carcinoma. J Immunol 154, 3932-3940.

Chu, B. C. F., Wahl, G. M. and Orgel, L. E/, *Nucleid Acids Research*, Vol 11, No 18 (1983).

Constant, P., Poquet, Y., Peyrat, M. A., Davodeau, F., Bonneville, M., and Fournie, J. J. (1995).

The antituberculous *Mycobacterium bovis* BCG vaccine is an attenuated mycobacterial producer of phosphorylated nonpeptidic antigens for human gamma delta T cells. Infect Immun 63, 4628-4633.

Corey E. J. and Katzenellenbogen J. A., J. Am. Chem. Soc. (1969), 91, 1851-1852

Corey E. J. and A. Venkateswarlu, J. Am. Chem. Soc. (1972), 94, 6190

Cox R. J., Gibson J. S., Mayo Martin M. B., *Chem BioChem*, 2002, 3, 874-886

Davisson et al., Methods Enzymol., 1984, 110, p 130-145.
Davisson et al., J. Org. Chem., 1986, 51, p 4768-4779.
Davisson et al., J. Org. Chem., 1987, 52, p 1794-1801.
Davodeau et al, (1993) J. Immunology 151(3): 1214-1223)
Espinosa, E., Belmant, C., Pont, F., Luciani, B., Poupot, R., Romagne, F., Brailly, H., Bonneville, M., and Fournie, J. J.

(2001a). Chemical synthesis and biological activity of bromohydrin pyrophosphate, a potent stimulator of human gamma delta T cells. J Biol Chem 276, 18337-18344.

Espinosa, E., Belmant, C., Sicard, H., Poupot, R., Bonneville, M., and Fournie, J. J. (2001b). Y2K+1 state-of-the-art on non-peptide phosphoantigens, a novel category of immunostimulatory molecules. Microbes Infect 3, 645-654.

Ferrarini, M., Heltai, S., Pupa, S. M., Mernard, S., and Zocchi, R. (1996). Killing of laminin receptor-positive human lung cancers by tumor infiltrating lymphocytes bearing gammadelta(+) t-cell receptors. J Natl Cancer Inst 88, 436-441.

Feurle, J., Espinosa, E., Eckstein, S., Pont, F., Kunzmann, V., Fournie, J. J., Herderich, M., and Wilhelm, M. (2002). *Escherichia coli* produces phosphoantigens activating human gamma delta T cells. J Biol Chem 277, 148-154.

Fisch, P., Moris, A., Rammensee, H. G., and Handgretinger, R. (2000). Inhibitory MHC class I receptors on gammadelta T cells in tumour immunity and autoimmunity. Immunol Today 21, 187-191.

Fournie, J. J., and Bonneville, M. (1996). Stimulation of gamma delta T cells by phosphoantigens. Res Immunol, $66^{th}$ Forum in Immunology, 147, 338-347.

Fox D. T. and Poulter C. D., *J. Org. Chem.* (2002), 67, 5009-5010

Fujimiya, Y., Suzuki, Y., Katakura, R., Miyagi, T., Yamaguchi, T., Yoshimoto, T., and Ebina, T. (1997). In vitro interleukin 12 activation of peripheral blood CD3(+)CD56(+) and CD3(+)CD56(−) gammadelta T cells from glioblastoma patients. Clin Cancer Res 3, 633-643.

Gober, H. J., Kistowska, M., Angman, L., Jeno, P., Mori, L., and De Libero, G. (2003). Human T cell receptor gammadelta cells recognize endogenous mevalonate metabolites in tumor cells. J Exp Med 197, 163-168.

Hayday, A. C. (2000). [gamma][delta] cells: a right time and a right place for a conserved third way of protection. Annu Rev Immunol 18, 975-1026.

Hintz et al. (2001). Identification of (E)-4-hydroxy-3-methylbut-2-enyl pyrophosphate as a major activator for human gammadelta T cells in *Escherichia coli*. FEBS Lett. 509 (2):317-22

Jomaa, H., Feurle, J., Luhs, K., Kunzmann, V., Tony, H. P., Herderich, M., and Wilhelm, M. (1999a). Vgamma9/Vdelta2 T cell activation induced by bacterial low molecular mass compounds depends on the 1-deoxy-D-xylulose 5-phosphate pathway of isoprenoid biosynthesis. FEMS Immunol Med Microbiol 25, 371-378.

Jomaa, H., Wiesner, J., Sanderbrand, S., Altincicek, B., Weidemeyer, C., Hintz, M., Turbachova, I., Eberl, M., Zeidler, J., Lichtenthaler, H. K., et al. (1999b). Inhibitors of the nonmevalonate pathway of isoprenoid biosynthesis as antimalarial drugs. Science 285, 1573-1576

Kato, Y., Tanaka, Y., Miyagawa, F., Yamashita, S., and Minato, N. (2001). Targeting of tumor cells for human gammadelta T cells by nonpeptide antigens. J Immunol 167, 5092-5098.

Knorre et al., Febs letters, 1976, 70, 105-108.

Kobayashi, H., Tanaka, Y., Yagi, J., Toma, H., and Uchiyama, T. (2001). Gamma/delta T cells provide innate immunity against renal cell carcinoma. Cancer Immunol Immunother 50, 115-124

Koppisch A. T. et al, *Organic Letters*, Vol. 2 No. 2 (2000) p 215-217

E. M. Kosower, B. Pazhenchevsky, H. Dodiuk, H. Kanety, and D. Faust, *J. Org. Chem.*, 46, 1668 (1981)

Kunzmann, V., Bauer, E., and Wilhelm, M. (1999). Gamma/delta T-cell stimulation by pamidronate. N Engl J Med 340, 737-738.

Lang, F., Peyrat, M. A., Constant, P., Davodeau, F., David-Ameline, J., Poquet, Y., Vie, H., Fournie, J. J., and Bonneville, M. (1995). Early activation of human V gamma 9V delta 2 T cell broad cytotoxicity and TNF production by nonpeptidic mycobacterial ligands. J Immunol 154, 5986-5994.

Leonard M. S, and al, *J. Org. Chem.* (2004), 69, 2526-2531

Liu et al., Angew. Chem. Int. Ed. 1999, 38, No 9, p 1245-1247.

Mitropoulos, D., Kooi, S., Rodriguez-Villanueva, J., and Platsoucas, C. D. (1994). Characterization of fresh (uncultured) tumour-infiltrating lymphocytes (TIL) and TIL-derived T cell lines from patients with renal cell carcinoma. Clin Exp Immunol 97, 321-327.

Miyashita et al, *J. Org. Chem.* 42 (1977) 3772-3774)

Miyagawa, F., Tanaka, Y., Yamashita, S., and Minato, N. (2001). Essential requirement of antigen presentation by monocyte lineage cells for the activation of primary human gamma delta T cells by aminobisphosphonate antigen. J Immunol 166, 5508-5514.

Moreau et al, (1986) J. Clin. Invest. 78:874)

Morita, C. T., Beckman, E. M., Bukowski, J. F., Tanaka, Y., Band, H., Bloom, B. R., Golan, D. E., and Brenner, M. B. (1995). Direct presentation of nonpeptide prenyl pyrophosphate antigens to human gamma delta T cells. Immunity 3, 495-507.

Nikolaides et al, Conversion Of Amines To Phosphoesters: Decyl Diethyl Phosphate, Organic Syntheses, CV 9, 194

Nilsson et al., Acta Chemica Scandinavia B 35, 1981, p 19-27.

Nilsson and Mosbach, Eur. J. Biochem., 1980, vol. 112, p 397-402.

Phan and Poulter, J. Org. Chem. (2001), 66, 6705-6710

Poccia, F., Cipriani, B., Vendetti, S., Colizzi, V., Poquet, Y., Battistini, L., Lopez-Botet, M., Fournie, J. J., and Gougeon, M. L. (1997a). CD94/NKG2 inhibitory receptor complex modulates both anti-viral and anti-tumoral responses of polyclonal phosphoantigen-reactive V gamma 9V delta 2 T lymphocytes. J Immunol 159, 6009-6017.

Poccia, F., Malkovsky, M., Gougeon, M. L., Bonneville, M., Lopez-Botet, M., Fournie, J. J., and Colizzi, V. (1997b). Gammadelta T cell activation or anergy during infections: the role of nonpeptidic TCR ligands and HLA class I molecules. J Leukoc Biol 62, 287-291.

Poquet, Y., Kroca, M., Halary, F., Stemnark, S., Peyrat, M. A., Bonneville, M., Fournie, J. J., and Sjostedt, A. (1998). Expansion of Vgamma9 Vdelta2 T cells is triggered by *Francisella* tularensis-derived phosphoantigens in tularemia but not after tularemia vaccination. Infect Immun 66, 2107-2114.

Rohmer, M., Knani, M., Simonin, P., Sutter, B., and Sahm, H. (1993). Isoprenoid biosynthesis in bacteria: a novel pathway for the early steps leading to isopentenyl diphosphate. Biochem J 295 (Pt 2), 517-524.

Rojas, R. E., Torres, M., Fournie, J. J., Harding, C. V., and Boom, W. H. (2002). Phosphoantigen presentation by macrophages to *mycobacterium tuberculosis*-reactive Vgamma9Vdelta2+ T cells: modulation by chloroquine. Infect Immun 70, 4019-4027.

Sato, E., Yoshikawa, M., and Kanaoka, Y. *Chem. Pharm. Bull,* 38(8), 2287-2289 (1990)

Seghal, D, Vijay, I. K., *Anal Biochem,* 218, 87 (1994)

Selin, L. K., Stewart, S., Shen, C., Mao, H. Q., and Wilkins, J. A. (1992). Reactivity of gamma delta T cells induced by the tumour cell line RPMI 8226: functional heterogeneity of clonal populations and role of GroEL heat shock proteins. Scand J Immunol 36, 107-117.

Shen, Y., Zhou, D., Qiu, L., Lai, X., Simon, M., Shen, L., Kou, Z., Wang, Q., Jiang, L., Estep, J., et al. (2002). Adaptive immune response of Vgamma2Vdelta2+ T cells during mycobacterial infections. Science 295, 2255-2258.

Sicard, H., Al Saati, T., Delsol, G., and Fournie, J. J. (2001). Synthetic phosphoantigens enhance human Vgamma9Vdelta2 T lymphocytes killing of non-Hodgkin's B lymphoma. Mol Med 7, 711-722.

Sturm, E., Braakman, E., Fisch, P., Vreugdenhil, R. J., Sondel, P., and Bolhuis, R. L. (1990). Human V gamma 9-V delta 2 T cell receptor-gamma delta lymphocytes show specificity to Daudi Burkitt's lymphoma cells. J Immunol 145, 3202-3208.

Tanaka, Y., Morita, C. T., Nieves, E., Brenner, M. B., and Bloom, B. R. (1995). Natural and synthetic non-peptide antigens recognized by human gamma delta T cells. Nature 375, 155-158.

Theodora W. Greene and Peter G. M. Wuts, "Protective Groups in Organic Synthesis", Third Edition, published by John Wiley & Sons, Inc. (1999)

Valentijn; van der Marel; Cohen; van Boom, *Syn. lett.* 1991, 663-664.

Valentijn, A. R. P. M.; O. van der Berg, G. A. van der Marel; L. H. Cohen; J. H. van Boom, *Tetrahedron*, vol. 51-7, 1995, 2099-2108.

Waschbusch et al. (1997). A new route to alpha-fluoroalkylphosphonates. J. Chem. Soc. Perkin Trans. 1, 1135-1139.

Wilhelm, M., Kunzmann, V., Eckstein, S., Reimer, P., Weissinger, F., Ruediger, T., and Tony, H. P. (2003). {gamma}{delta} T cells for immune therapy of patients with lymphoid malignancies. Blood, 102(1), 200-6.

Yamaguchi, T., Fujimiya, Y., Suzuki, Y., Katakura, R., and Ebina, T. (1997). A simple method for the propagation and purification of gamma delta T cells from the peripheral blood of glioblastoma patients using solid-phase anti-CD3 antibody and soluble IL-2. J Immunol Methods 205, 19-28.

Zhang Donglu and Poulter C. Dale "Analysis and Purification of Phosphorylated Isoprenoids by Reversed-Phase HPLC", *Analytical Biochemistry*, vol. 213, 356-361 (1993)

Zheng, B., Lam, C., Im, S., Huang, J., Luk, W., Lau, S. Y., Yau, K. K., Wong, C., Yao, K., and Ng, M. H. (2001a). Distinct tumour specificity and IL-7 requirements of CD56(−)and CD56(+) subsets of human gamma delta T cells. Scand J Immunol 53, 40-48.

Zheng, B. J., Chan, K. W., Im, S., Chua, D., Sham, J. S., Tin, P. C., He, Z. M., and Ng, M. H. (2001b). Anti-tumor effects of human peripheral gammadelta T cells in a mouse tumor model. Int J Cancer 92, 421-425.

The invention claimed is:

1. A γδ T cell activator of formula:

$$R_5-W=\underset{R_7}{\overset{R_3}{C}}-\underset{R_4}{\overset{}{C}}-A-\left[\underset{O^-Cat^+}{\overset{O}{\overset{\|}{P}}}-B\right]_m-\underset{O^-Cat^+}{\overset{O}{\overset{\|}{P}}}-Y; \quad (I)$$

$$\underset{R_5}{\overset{R_6}{\diagdown}}C=\underset{R_7}{\overset{}{C}}-\underset{R_4}{\overset{R_3}{C}}-A-\left[\underset{O^-Cat^+}{\overset{O}{\overset{\|}{P}}}-B\right]_m-\underset{O^-Cat^+}{\overset{O}{\overset{\|}{P}}}-Y; \quad (II)$$

$$R_5-N=\underset{R_7}{\overset{R_3}{C}}-\underset{R_4}{\overset{}{C}}-A-\left[\underset{O^-Cat^+}{\overset{O}{\overset{\|}{P}}}-B\right]_m-\underset{O^-Cat^+}{\overset{O}{\overset{\|}{P}}}-Y; \text{ or} \quad (III)$$

$$R_5-W=\underset{CH_3}{\overset{R_3}{C}}-\underset{R_4}{\overset{}{C}}-A-\left[\underset{O^-Cat^+}{\overset{O}{\overset{\|}{P}}}-B\right]_m-\underset{O^-Cat^+}{\overset{O}{\overset{\|}{P}}}-Y, \quad (V)$$

wherein Cat$^+$ represents one or more cation, that can be the same or different, selected from proton(s), organic cation(s) or mineral cation(s);

m is an integer from 1 to 3;

B is O, NH;

A is O, NH, CHF, CF$_2$ or CH$_2$;

W is C—R$_6$ or N;

R$_7$ is a (C$_1$-C$_3$)alkyl group, CF$_3$, CH$_2$F or CF$_2$H;

R$_3$, R$_4$, and R$_6$ identical or different, are a hydrogen or a (C$_1$-C$_3$)alky group;

R$_5$ is an (C$_2$-C$_3$)acyl, an aldehyde, an (C$_1$-C$_3$)alcohol, or an (C$_2$-C$_3$)ester; and, Y is O$^-$Cat$^+$, a C$_1$-C$_3$ alky group, or a group -A-R, wherein R is a linear, branched, or cyclic, aromatic or non-aromatic, saturated or unsaturated, C$_1$-C$_{50}$ hydrocarbon group, wherein said hydrocarbon group can be interrupted by at least one heteroatom or is uninterrupted and said hydrocarbon group comprises an alkyl, an alkylenyl or an alkynyl which can be substituted by one or several substituents selected from the group consisting of: an alkyl, an alkylenyl, an alkylnyl, an epoxyalkyl, an aryl, an heterocycle, an alkoxy, an acyl, an alcohol, a carboxylic group (—COOH), an ester, an amine, an amino group (—NH$_2$), an amide (—CONH$_2$), an imine, a nitrile, an hydroxyl (—OH), a aldehyde group (—CHO), an halogen, an halogenoalkyl, a thiol (—SH), a thioalkyl, a sulfone, a sulfoxide, and a combination thereof.

2. The γδ T cell activator according to claim 1, wherein said activator is a compound of formula (VI):

$$HOCH_2-W=\underset{CH_3}{\overset{R_3}{C}}-\underset{R_4}{\overset{}{C}}-A-\left[\underset{O\text{-}Cat+}{\overset{O}{\overset{\|}{P}}}-B\right]_m-\underset{O\text{-}Cat+}{\overset{O}{\overset{\|}{P}}}-Y. \quad (VI)$$

wherein Cat$^+$ represents one or more cation, that can be the same or different, selected from proton(s), organic cation(s) or mineral cation(s);

m is an integer from 1 to 3;

B is O, NH;

A is O, NH, CHF, CF$_2$ or CH$_2$;

W is C—R$_6$ or N;

R$_3$, R$_4$ and R$_6$ identical or different, are a hydrogen or a (C$_1$-C$_3$)alky group;

Y is O$^-$Cat$^-$, a C$_1$-C$_3$ alky group, or a group -A-R, wherein R is a linear, branched, or cyclic, aromatic or non-aromatic, saturated or unsaturated, C$_1$-C$_{50}$ hydrocarbon group, wherein said hydrocarbon group can be interrupted by at least one heteroatom or is uninterrupted and said hydrocarbon group comprises an alkyl, an alkylenyl or an alkynyl which can be substituted by one or several substituents selected from the group consisting of: an alkyl, an alkylenyl, an alkylnyl, an epoxyalkyl, an aryl, an heterocycle, an alkoxy, an acyl, an alcohol, a carboxylic group (—COOH), an ester, an amine, an amino group (—NH$_2$), an amide (—CONH$_2$), an imine, a nitrile, an hydroxyl (—OH), a aldehyde group (—CHO), an halogen, an halogenoalkyl, a thiol (—SH), a thioalkyl, a sulfone, a sulfoxide, and a combination thereof.

3. The γδ T cell activator according to claim 1, wherein $R_5$ is —$CH_2$—OH, —CHO, —CO—$CH_3$ or —CO—$OCH_3$.

4. The γδ T cell activator according to claim 3, wherein $R_5$ is —$CH_2$—OH.

5. The γδ T cell activator according to claim 1, wherein $R_7$ is —$CH_3$—, $CH_2F$, $CF_2H$ or $CF_3$.

6. The γδ T cell activator according to claim 3, wherein $R_7$ is —$CH_3$—, $CH_2F$, $CF_2H$ or $CF_3$.

7. The γδ T cell activator according to claim 5, wherein $R_7$ is —$CH_3$.

8. The γδ T cell activator according to claim 6, wherein $R_7$ is —$CH_3$.

9. The γδ T cell activator according to claim 1, wherein A is O.

10. The γδ T cell activator according to claim 1, wherein A is NH.

11. The γδ T cell activator according to claim 1, wherein A is CHF, $CF_2$, $CH_2$.

12. The γδ T cell activator according to claim 1, wherein B is O.

13. The γδ T cell activator according to claim 1, wherein m is 1.

14. The γδ T cell activator according to claim 1, wherein Y is $O^-Cat^+$ or a nucleoside.

15. The γδ T cell activator according to claim 2, wherein said activator is a compound of formula (XII):

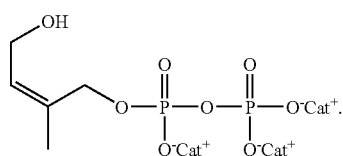
(XII)

16. The γδ T cell activator according to claim 2, wherein said activator is a compound of formula (XIII):

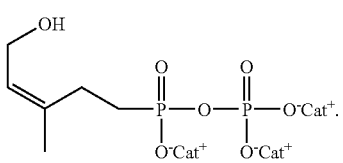
(XIII)

17. The γδ T cell activator according to claim 2, wherein said activator is a compound of formula (XIV):

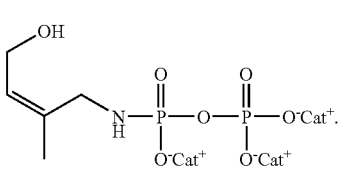
(XIV)

18. A composition comprising a γδ T cell activator of formula:

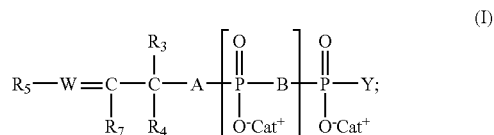
(I)

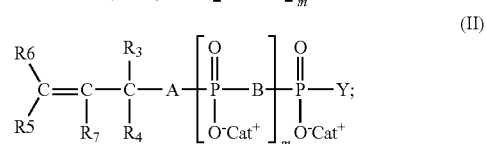
(II)

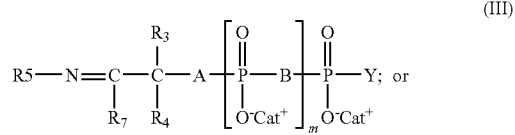
(III)

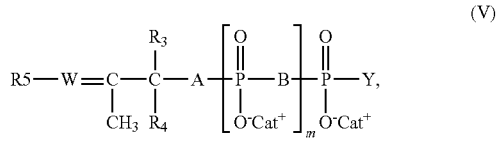
(V)

wherein $Cat^-$ represents one or more cation, that can be the same or different, selected from proton(s), organic cation(s) or mineral cation(s);

m is an integer from 1 to 3;

B is O, NH;

A is O, NH, CHF, $CF_2$ or $CH_2$;

W is C—$R_6$ or N;

$R_7$ is a ($C_1$-$C_3$)alkyl group, or $CF_3$, $CH_2F$ or $CF_2H$;

$R_3$, $R_4$, and $R_6$ identical or different, are a hydrogen or a ($C_1$-$C_3$)alky group; $R_5$ is an ($C_2$-$C_3$)acyl, an aldehyde, an ($C_1$-$C_3$)alcohol, or an ($C_2$-$C_3$)ester; and Y is $O^-Cat^+$, a $C_1$-$C_3$ alkyl group, or a group -A-R, wherein R is a linear, branched, or cyclic, aromatic or non-aromatic, saturated or unsaturated, $C_1$-$C_{50}$ hydrocarbon group, wherein said hydrocarbon group can be interrupted by at least one heteroatom or is uninterrupted and said hydrocarbon group comprises an alkyl, an alkylenyl or an alkynyl which can be substituted by one or several substituents selected from the group consisting of: an alkyl, an alkylenyl, an alkylnyl, an epoxyalkyl, an aryl, an heterocycle, an alkoxy, an acyl, an alcohol, a carboxylic group (—COOH), an ester, an amine, an amino group (—$NH_2$), an amide (—$CONH_2$), an imine, a nitrile, an hydroxyl (—OH), a aldehyde group (—CHO), an halogen, an halogenoalkyl, a thiol (—SH), a thioalkyl, a sulfone, a sulfoxide, and a combination thereof.

19. A method of treating an infectious disease comprising that administration of a composition comprising a compound according to claim 1 to a subject suffering from an infectious disease.

20. A method of activating γδ T cell, the method comprising bringing a γδ T cell into contact with a γδ T cell activator according to claim 1.

21. The method according to claim 20, wherein the γδ T cell is brought into contact with said γδ T cell activator in vitro.

22. The composition according to claim 18, wherein said activator is a compound of formula (XII'):

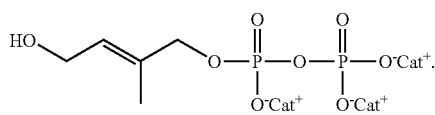

23. The composition according to claim 18, wherein said activator is a compound of formula (XIII'):

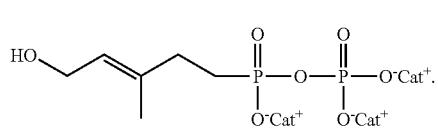

24. The composition according to claim 18, wherein said activator is a compound of formula (XIV'):

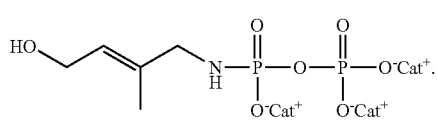

25. The method according to claim 19, wherein said infectious disease is caused by a virus selected from HIV, CMV, EBV, Influenza virus, HPV, HCV and HBV or by a pathogen causing a disease selected from tuberculosis, malaria, tularemia and colibacillosis.

26. The method according to claim 19, wherein said compound is a compound of formula (XII'):

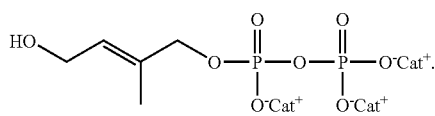

27. The method according to claim 19, wherein said compound is a compound of formula (XIII'):

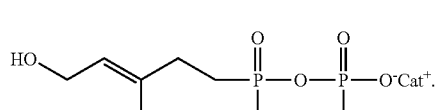

28. The method according to claim 19, wherein said compound is a compound of formula (XIV'):

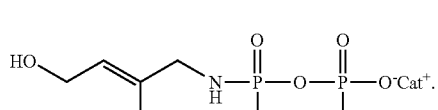

29. The method according to claim 19, wherein said compound is administered in a dosage between about 1 µg/kg and 1.2 g/kg.

30. The method according to claim 19, wherein said compound is administered conjointly with other active agents.

31. The method according to claim 30, wherein said active agent is interleukin-2 (IL-2).

32. A method for enhancing the immune response against an antigen in a mammal, involving the conjoint immunization of the mammal with:

a) a composition comprising an antigen; and b) an adjuvant comprising a compound according to claim 1.

33. The method according to claim 32, wherein said compound is a compound of formula

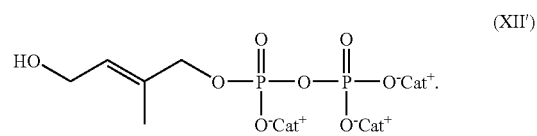

34. The method according to claim 32, wherein said compound is a compound of formula (XIII'):

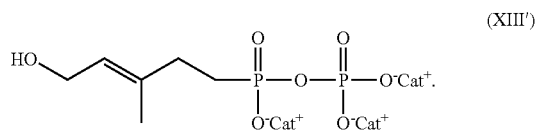

35. The method according to claim 32, wherein said compound is a compound of formula (XIV'):

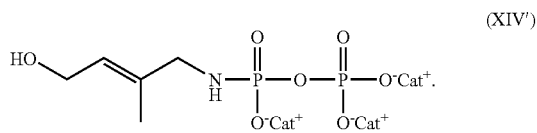

36. A kit comprising an antigen and a compound according to claim 1.

37. The kit according to claim 36, wherein said compound is a compound of formula

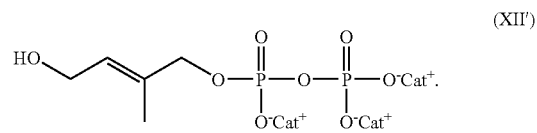

38. The kit according to claim 36, wherein said compound is a compound of formula (XIII'):

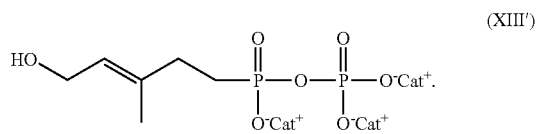

39. The kit according to claim 36, wherein said compound is a compound of formula (XIV'):
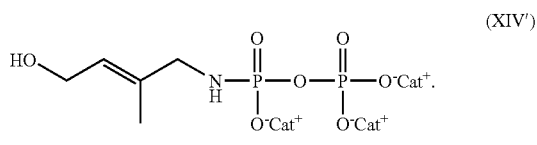
(XIV')
40. The method according to claim 20, wherein said compound is a compound of formula (XII):
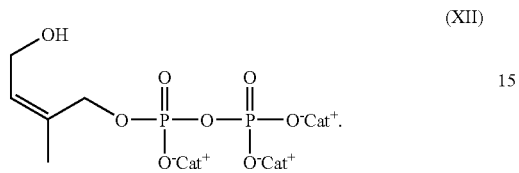
(XII)
41. The method according to claim 20, wherein said compound is a compound of formula (XIII):
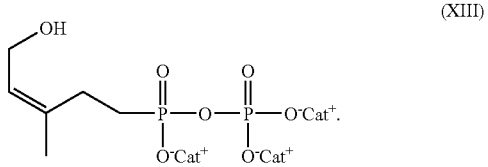
(XIII)
42. The method according to claim 20, wherein said compound is a compound of formula (XIV):
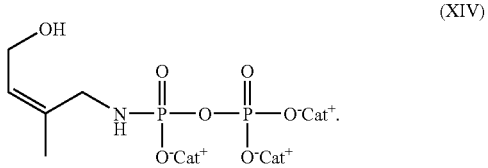
(XIV)
* * * * *

UNITED STATES PATENT AND TRADEMARK OFFICE
CERTIFICATE OF CORRECTION

PATENT NO.       : 7,683,045 B2                                    Page 1 of 2
APPLICATION NO.  : 11/817450
DATED            : March 23, 2010
INVENTOR(S)      : Christian Belmant It is certified that error appears in the above-identified patent and that said Letters Patent is hereby corrected as shown below:

Column 14,
Line 62, "B is OIn one" should read --B is O. In one--.

Column 21,
Lines 36-40, should read

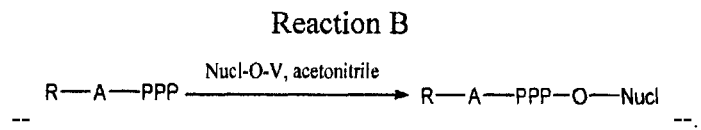

Column 24,
Lines 32-35,

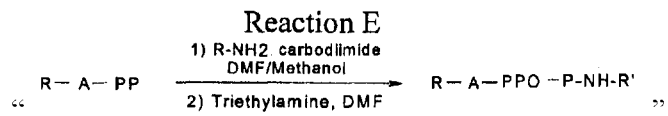

should read

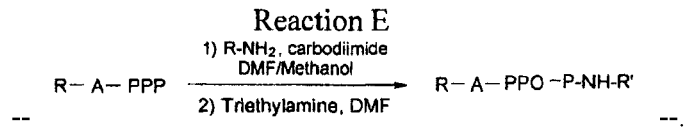

Signed and Sealed this

Twenty-ninth Day of June, 2010

David J. Kappos
*Director of the United States Patent and Trademark Office*

Column 40,
Line 29, "an alkylnyl" should read --an alkynyl--.
Line 63, "an alkylnyl" should read --an alkynyl--.

Column 42,
Line 28, "wherein Cat⁻ represents" should read --wherein $Cat^+$ represents--.
Line 49, "an alkylnyl" should read --an alkynyl--.